(12) United States Patent
Elliott et al.

(10) Patent No.: US 7,956,224 B2
(45) Date of Patent: Jun. 7, 2011

(54) PALLADIUM CATALYZED HYDROGENATION OF BIO-OILS AND ORGANIC COMPOUNDS

(75) Inventors: Douglas C. Elliott, Kennewick, WA (US); Jianli Hu, Richland, WA (US); Todd R. Hart, Kennewick, WA (US); Gary G. Neuenschwander, Burbank, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 12/140,929

(22) Filed: Jun. 17, 2008

(65) Prior Publication Data

US 2009/0113787 A1  May 7, 2009

Related U.S. Application Data

(63) Continuation of application No. 11/759,075, filed on Jun. 6, 2007, now Pat. No. 7,425,657.

(51) Int. Cl.
*C07C 37/00* (2006.01)
*C07C 35/06* (2006.01)

(52) U.S. Cl. ..................................... 568/869
(58) Field of Classification Search ............... 568/869
See application file for complete search history.

(56) References Cited

U.S. PATENT DOCUMENTS

| | | | |
|---|---|---|---|
| 4,320,241 | A | 3/1982 | Frankiewicz |
| 4,398,039 | A | 8/1983 | Pesa et al. |
| 4,764,627 | A | 8/1988 | Diebold et al. |
| 4,777,303 | A | 10/1988 | Kitson et al. |
| 4,795,841 | A | 1/1989 | Elliott et al. |
| 4,804,791 | A | 2/1989 | Kitson et al. |
| 4,826,795 | A | 5/1989 | Kitson et al. |
| 4,985,572 | A | 1/1991 | Kitson et al. |
| 4,990,655 | A | 2/1991 | Kitson et al. |
| 5,149,680 | A | 9/1992 | Kitson et al. |
| 5,883,266 | A | 3/1999 | Elliott et al. |
| 6,479,677 | B1 | 11/2002 | Ahmed |
| 7,425,657 | B1* | 9/2008 | Elliott et al. ............... 568/667 |

FOREIGN PATENT DOCUMENTS

| | | |
|---|---|---|
| CN | 1562477 | 3/2004 |
| RU | 2292952 | 2/2007 |
| WO | WO2007/003709 | 1/2007 |

OTHER PUBLICATIONS

Elliott et al., "Hydrogenation of bio-oil for chemical and fuel production," Science in Thermal and Chemical Biomass Conversion, CPL Press, Newbury, pp. 1536-1546 (2006).

Elliott et al., "Low Temperature Catalytic Gasification of Chemical Manufacturing Wastewaters, 1995-1998 Final Report," PNNL-11992 (Sep. 1998).

Scholze, "Long-Term Stability, Catalytic Upgrading, and Application of Pyrolysis Oils—Improving the Properties of a Potential Substitute for Fossil Fuels," Dissertation, pp. 1-150, Hamburg (2002).

Elliott et al., "Chemical Processing in High-Pressure Aqueous Environments. 8. Improved Catalysts for Hydrothermal Gasification," Ind. Eng. Chem. Res. 45, pp. 3776-3781 (published on web Apr. 26, 2006).

Elliott et al., (1987) Hydrotreating biomass liquids to produce hydrocarbon fuels, In: Energy from Biomass and Waste X. (Ed. D. L. Klass), pp. 765-784. Institute of Gas Technology, Chicago.

Laurent, "Etude et controle des reactions d'hydrodesoxygenation lors de l'hydroraffinage des huiles de pyrolse de la biomasse," Dissertation, pp. 133-137, Hamburg (1993). (in English).

Elliott et al., (1988) Catalytic upgrading of biomass pyrolysis oils, In: Research in Thermochemical Biomass Conversion, (Eds. A.V. Bridgwater & J. L. Kuester), pp. 883-895, Elsevier Applied Science, London.

Baldauf et al., "Upgrading of Flash Pyrolysis Oil and Utilization in Refineries," Biomass and Bioenergy, 7, pp. 237-244 (1994).

Meier et al., "Upgrading of Bio-Oils and Flash Pyrolysis of CCB-Treated Wood Waste," Proceedings of the 2nd EU-Canada Workshop on Thermal Biomass Processing, CPL Press, pp. 102-112 (1996).

Centano et al., "Behavior of Catalysts Supported on Carbon in Hydrodeoxygenation Reactions," pp. 589-601, Blackie Academic and Scientific, London (1997).

Machine Translation of CN 1562477, Jul. 26, 2010.

International Search Report and Written Opinion from PCT/US2008/065884, mailed Jun. 18, 2009.

Elliott, "Historical Developments in Hydroprocessing Bio-oils," Energy & Fuels, pp. 1792-1815 (2007).

Elliott et al., "Liquid Fuels by Low-Severity Hydrotreating of Biocrude," Developments in Thermochemical Biomass Conversion, pp. 611-621 (19996).

Huber et al., "An overview of aqueous-phase catalytic processes for production of hydrogen and alkanes in a biorefinery," Catalysis Today 111, pp. 119-132 (2006).

Rioche et al., "Steam reforming of model compounds and fast pyrolysis bio-oil on supported noble metal catalysts," Applied Catal B: Environmental 61, pp. 130-139 (2005).

* cited by examiner

*Primary Examiner* — Elvis O Price
(74) *Attorney, Agent, or Firm* — Derek H. Maughan; Frank Rosenberg

(57) ABSTRACT

The invention provides palladium-catalyzed hydrogenations of bio-oils and certain organic compounds. Experimental results have shown unexpected and superior results for palladium-catalyzed hydrogenations of organic compounds typically found in bio-oils.

15 Claims, 24 Drawing Sheets

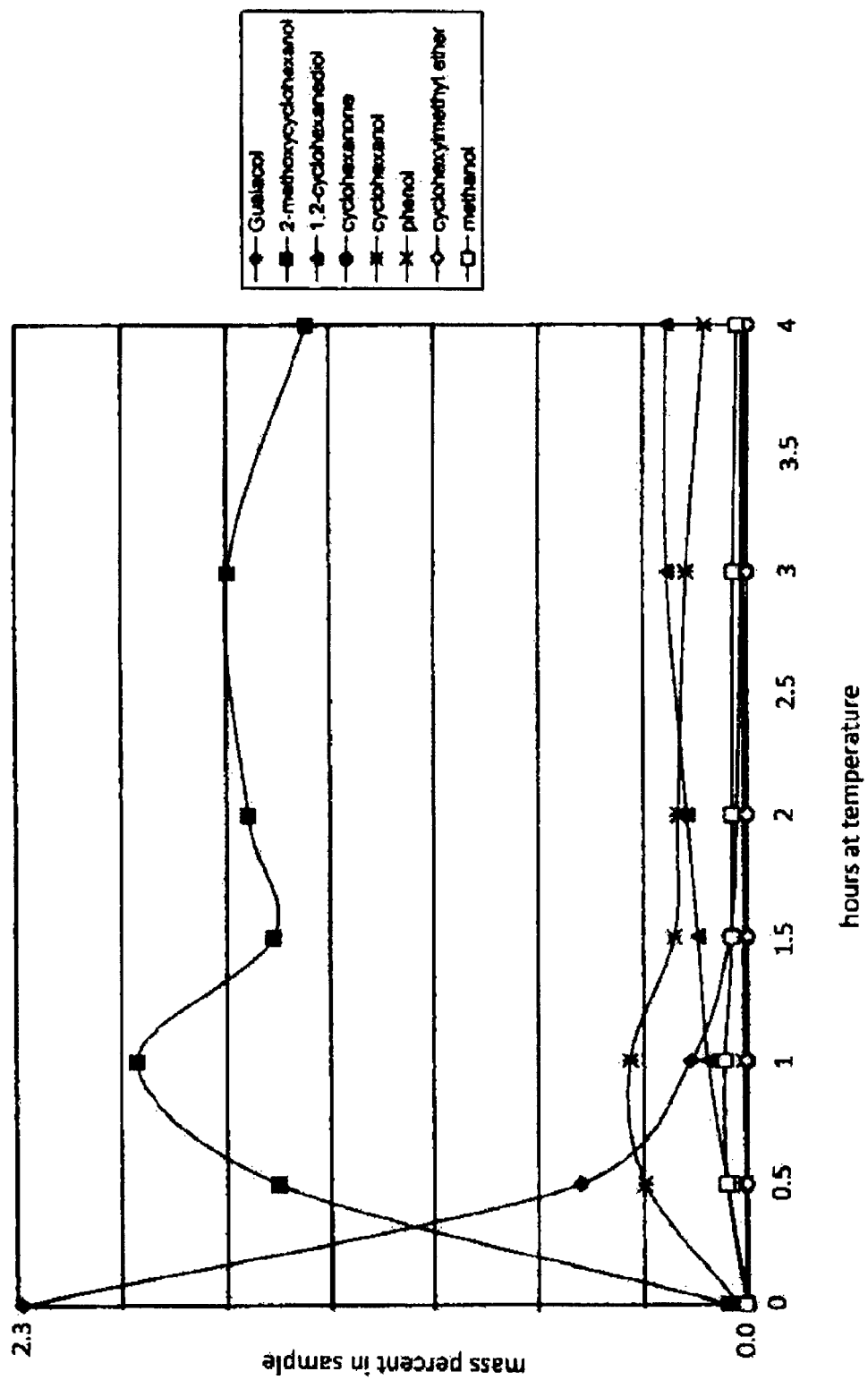
Figure 1. Guaiacol Hydrogenation/Ru-150C

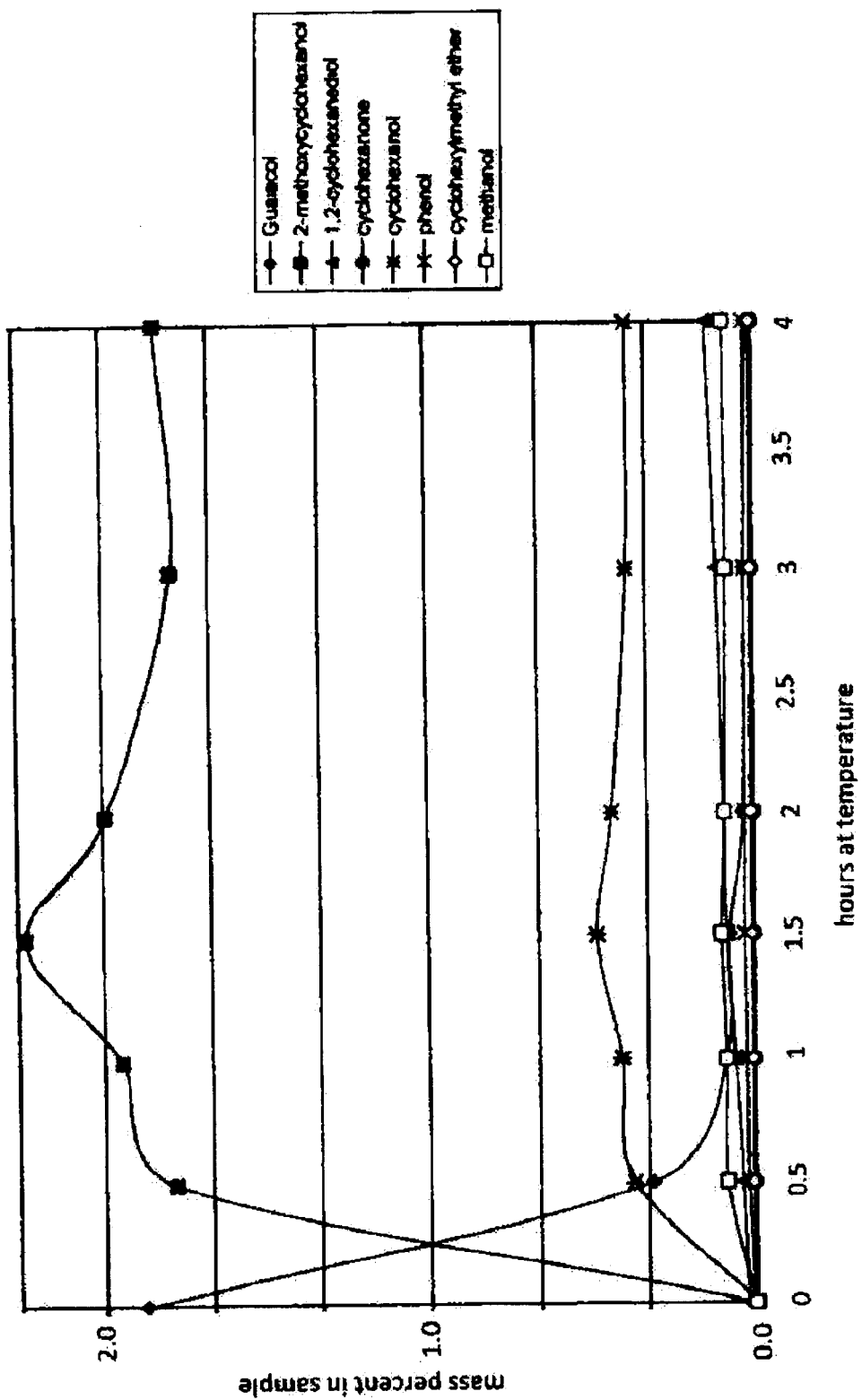

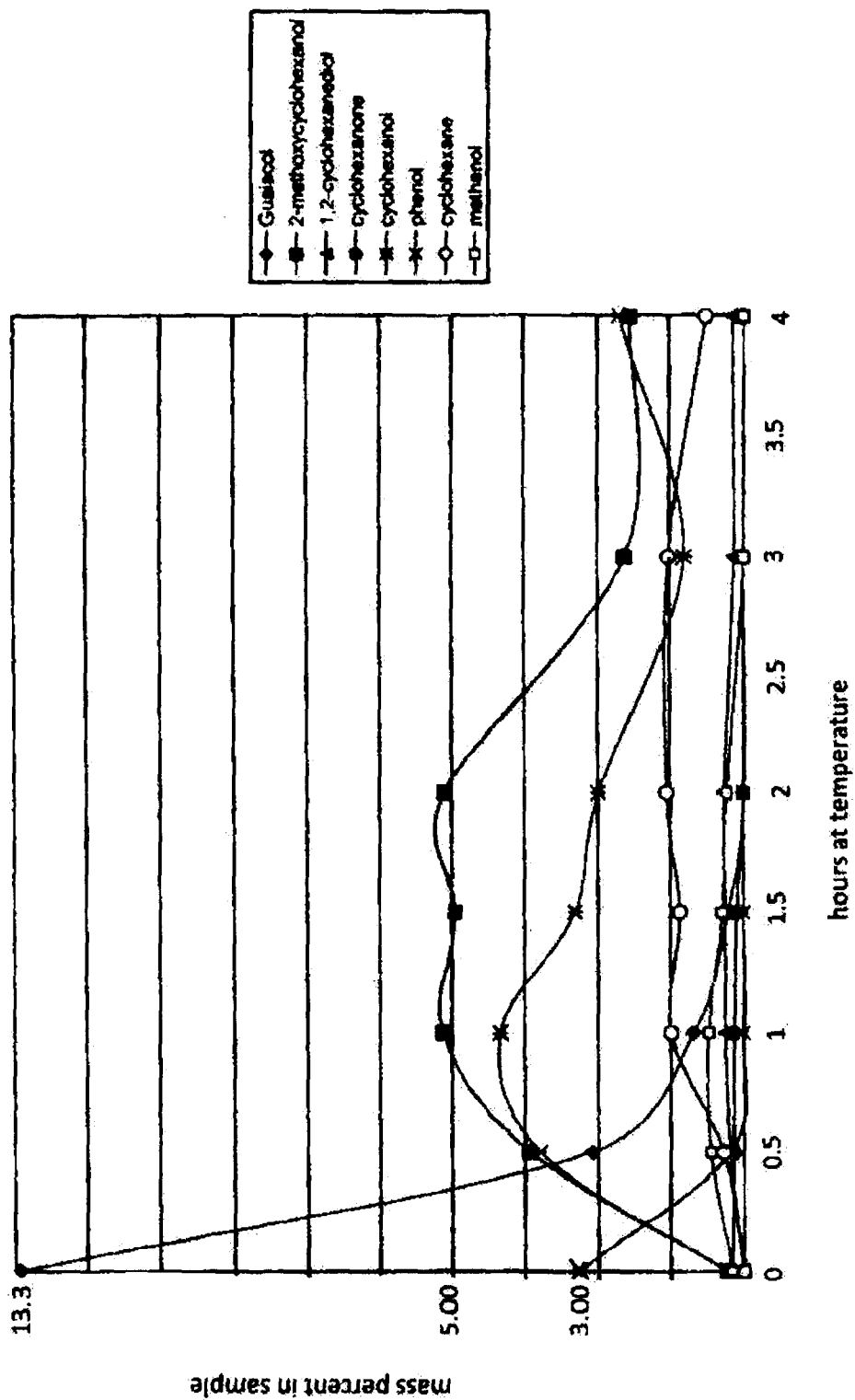

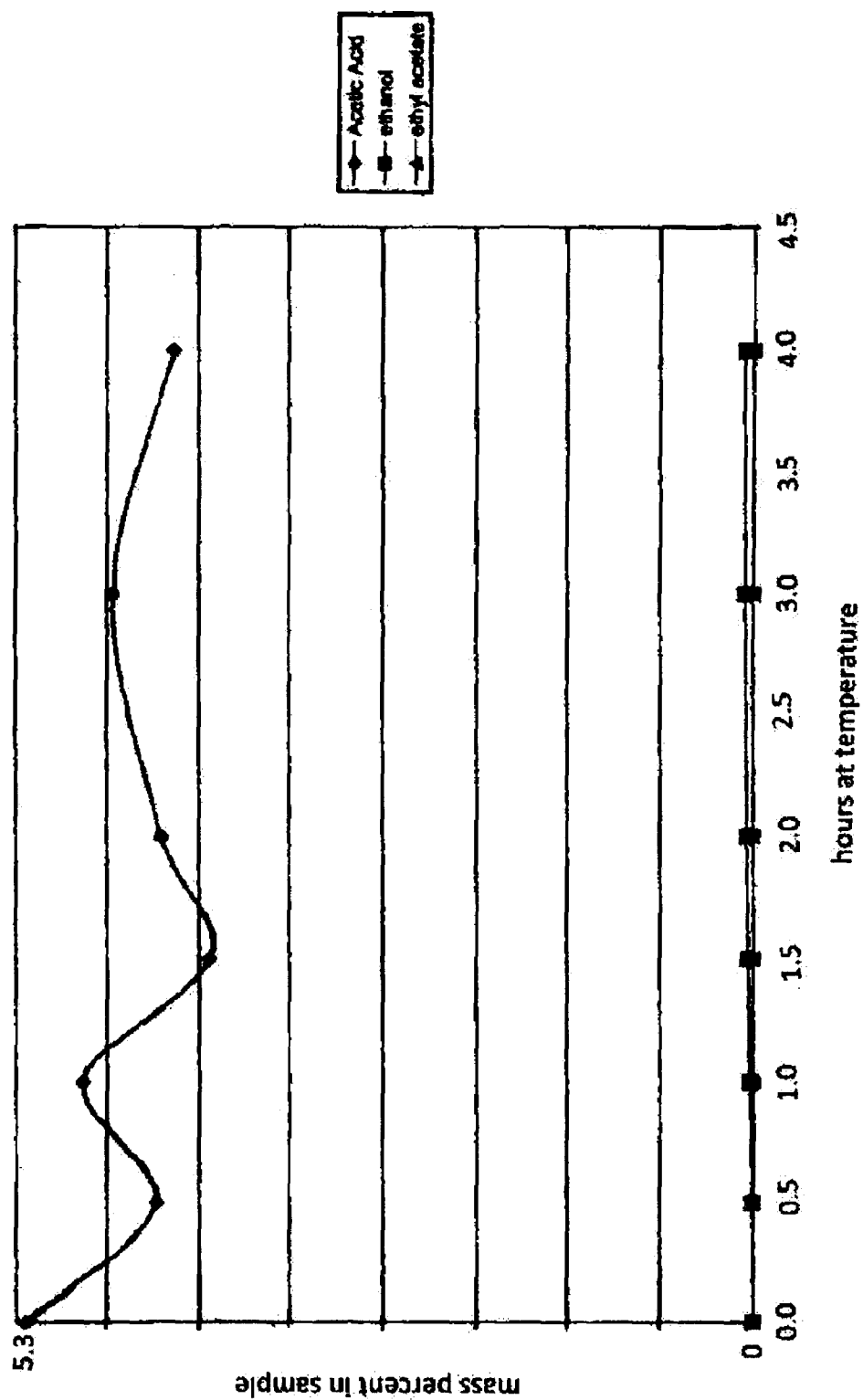

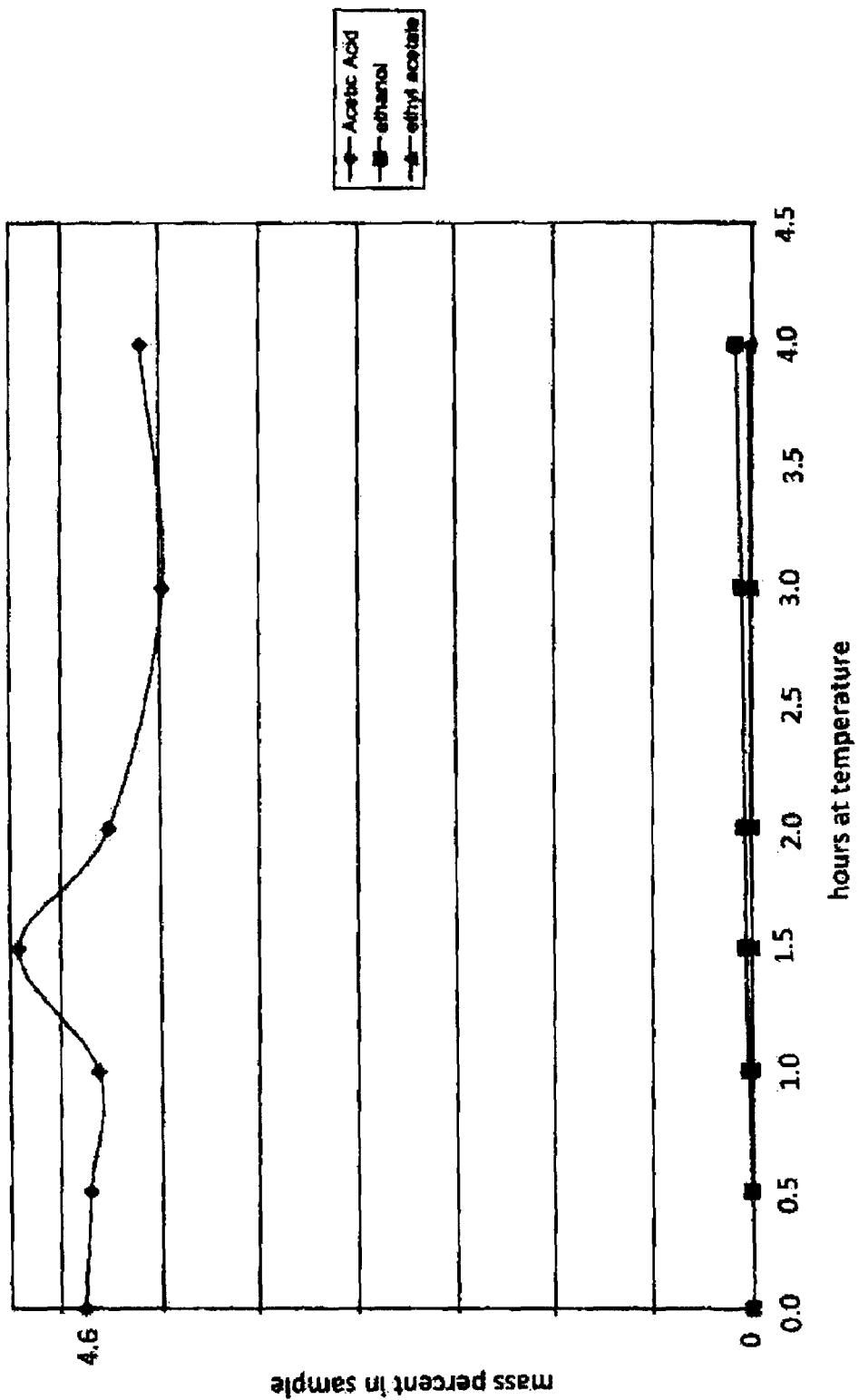

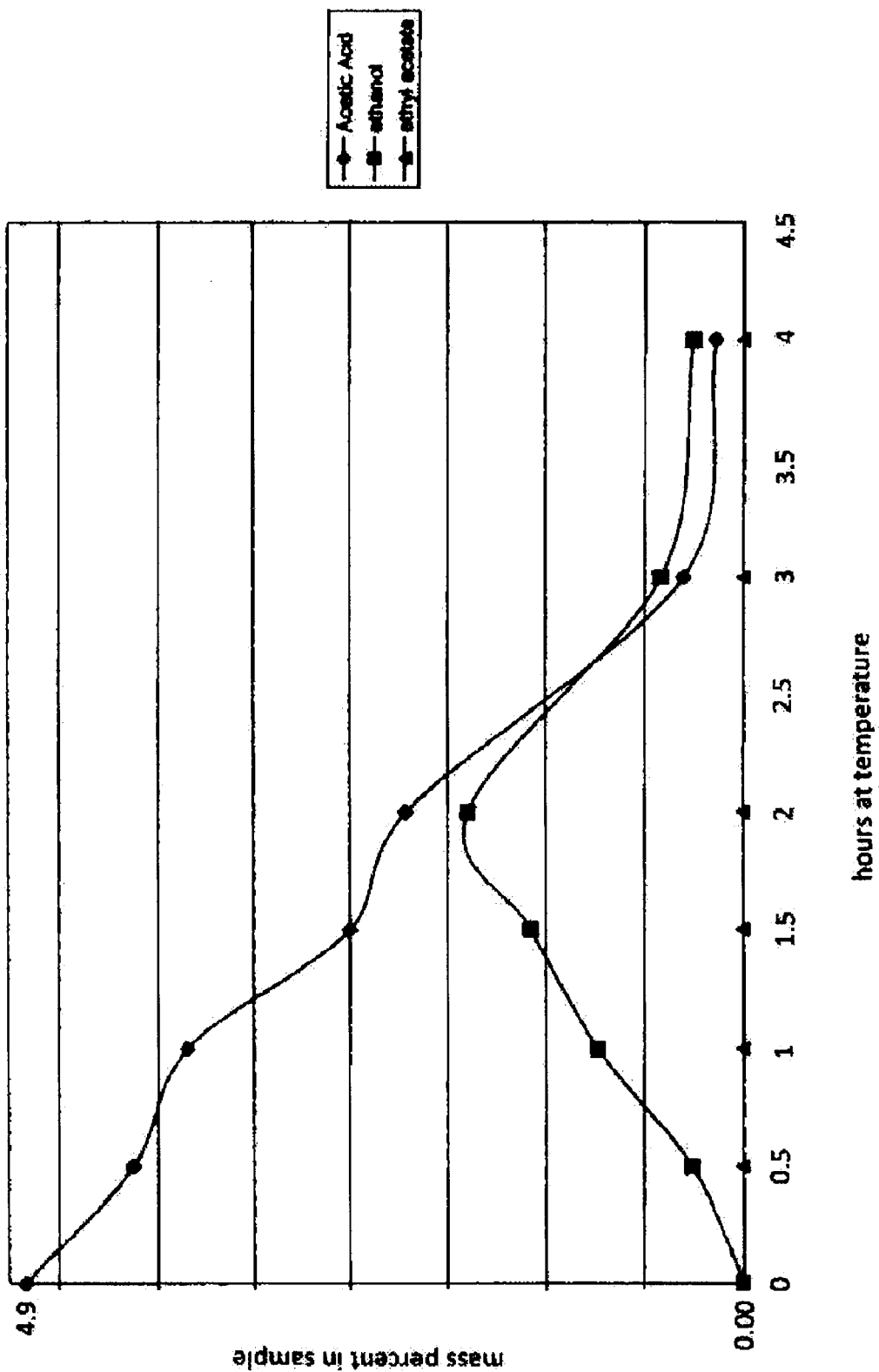

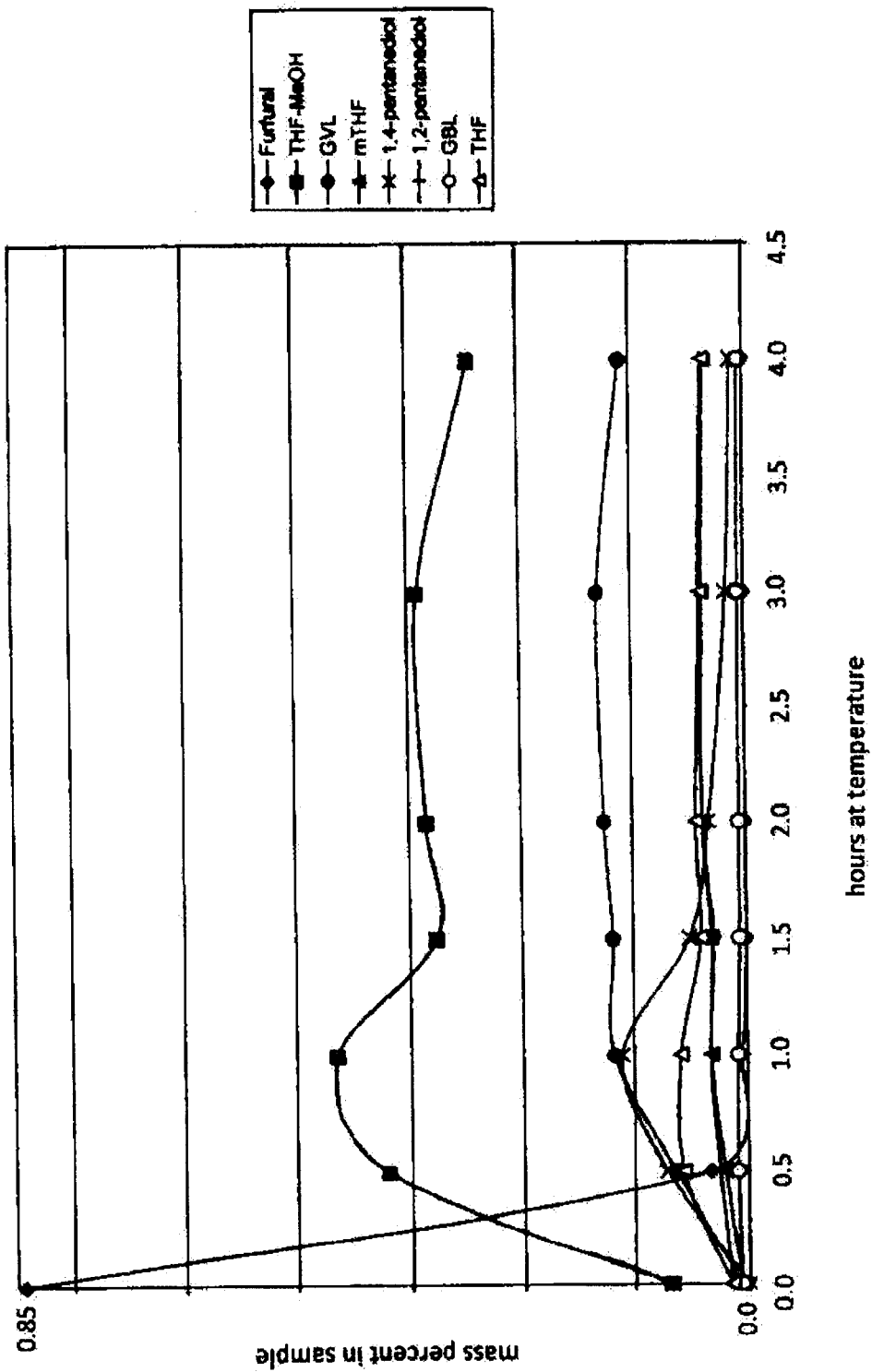
Figure 7. Furfural Hydrogenation to Cyclic Ethers/Ru-150C

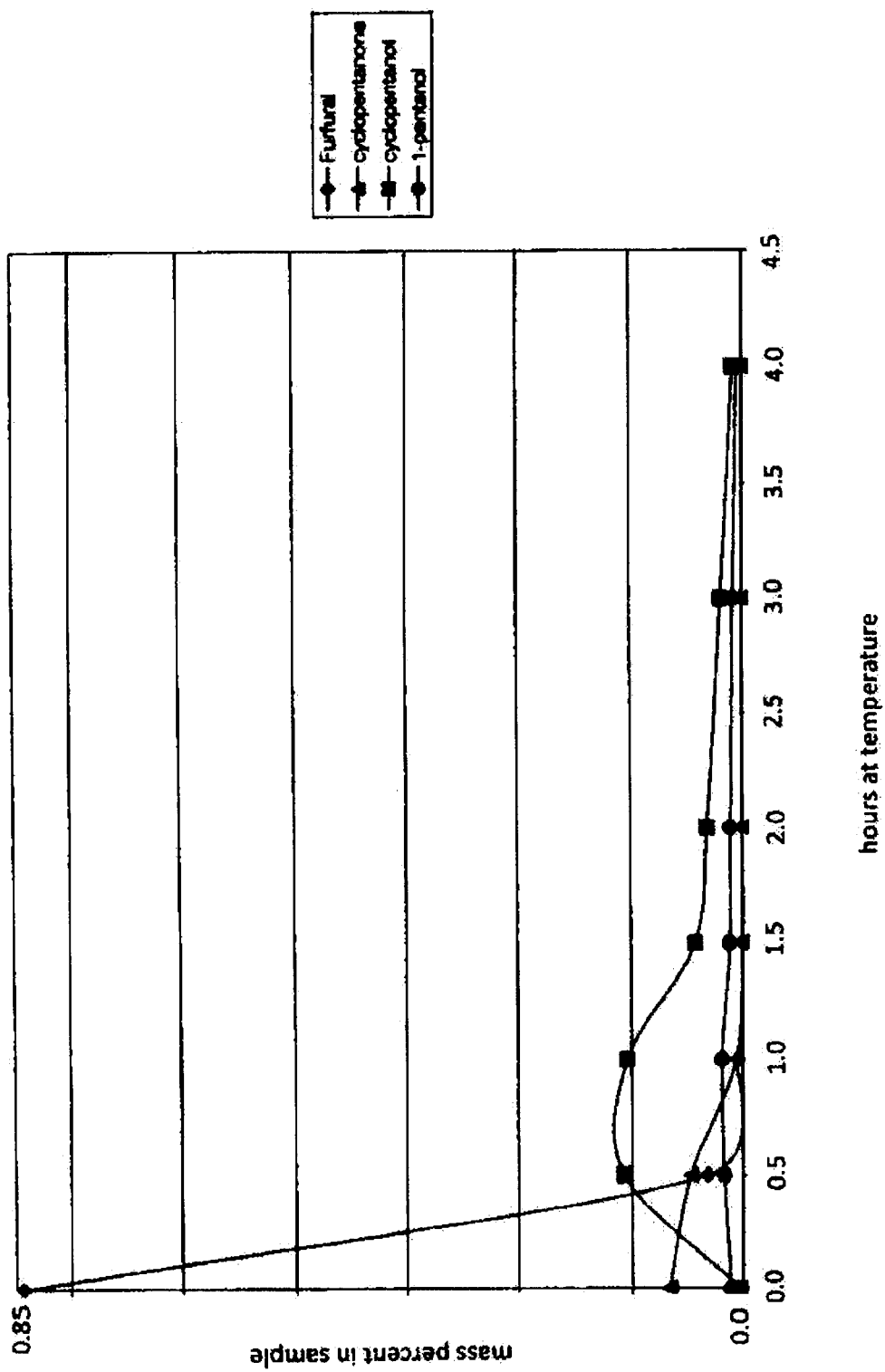

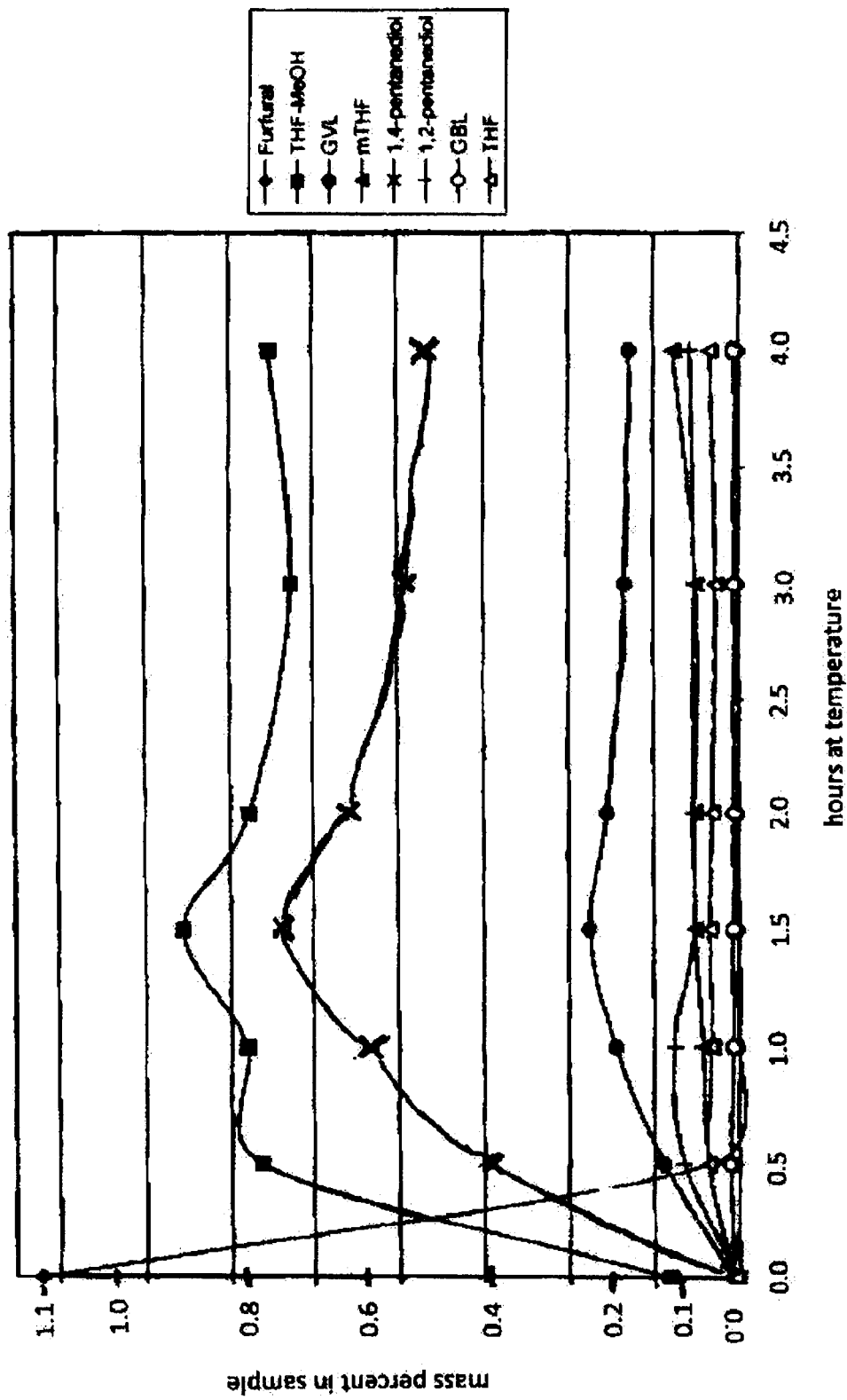

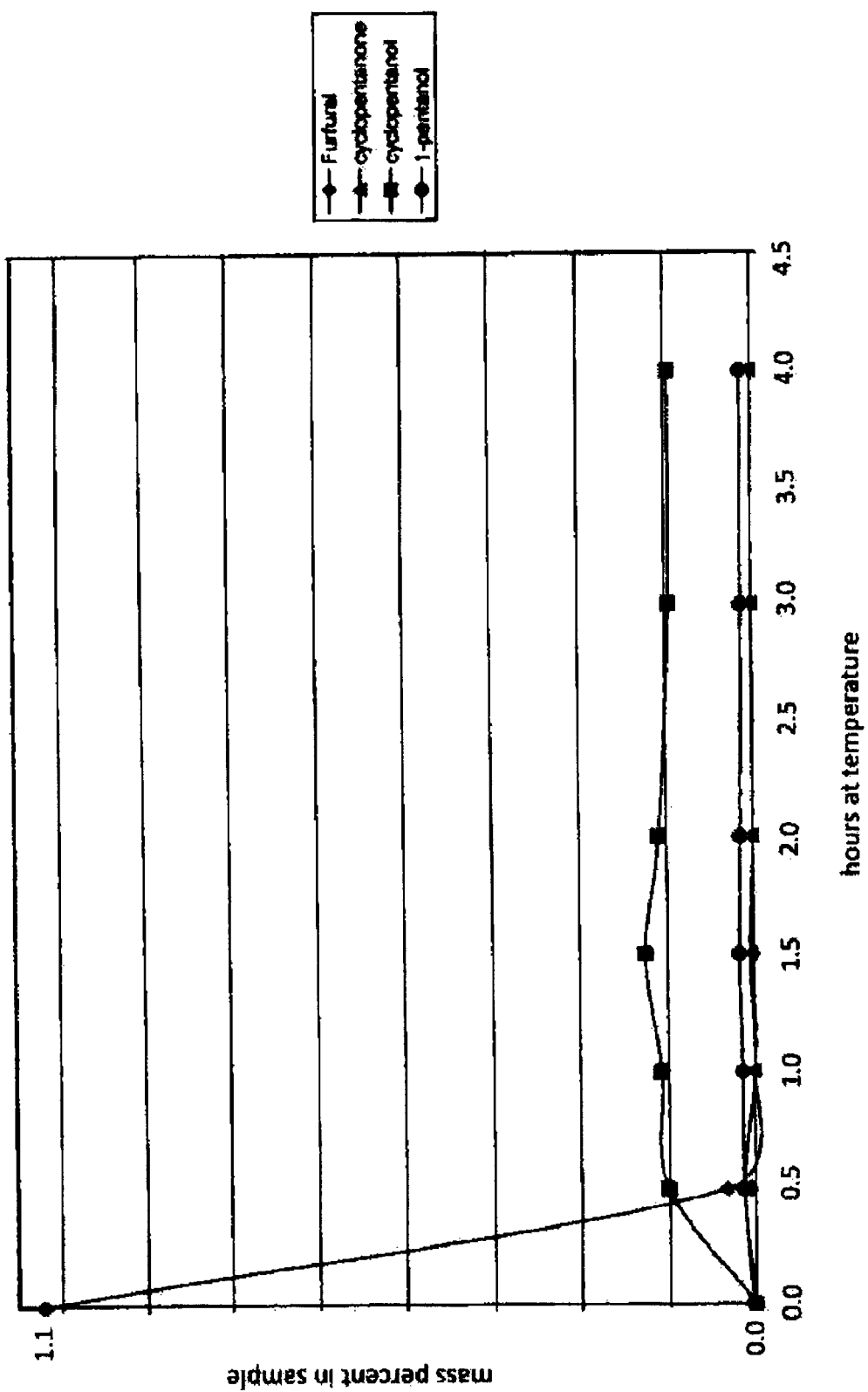
Figure 10. Furfural Hydrogenation to Alcohols/Ru-200C

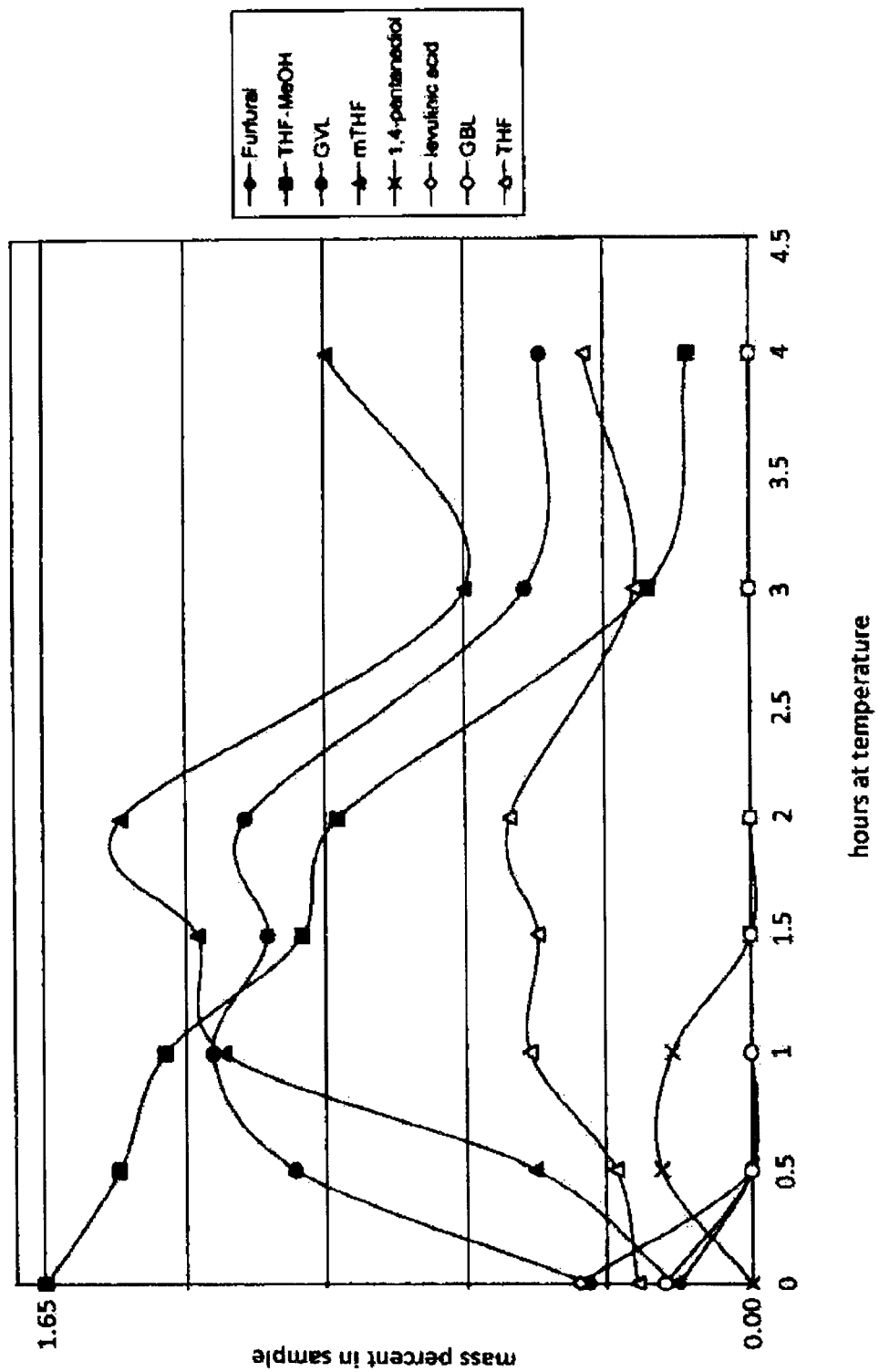

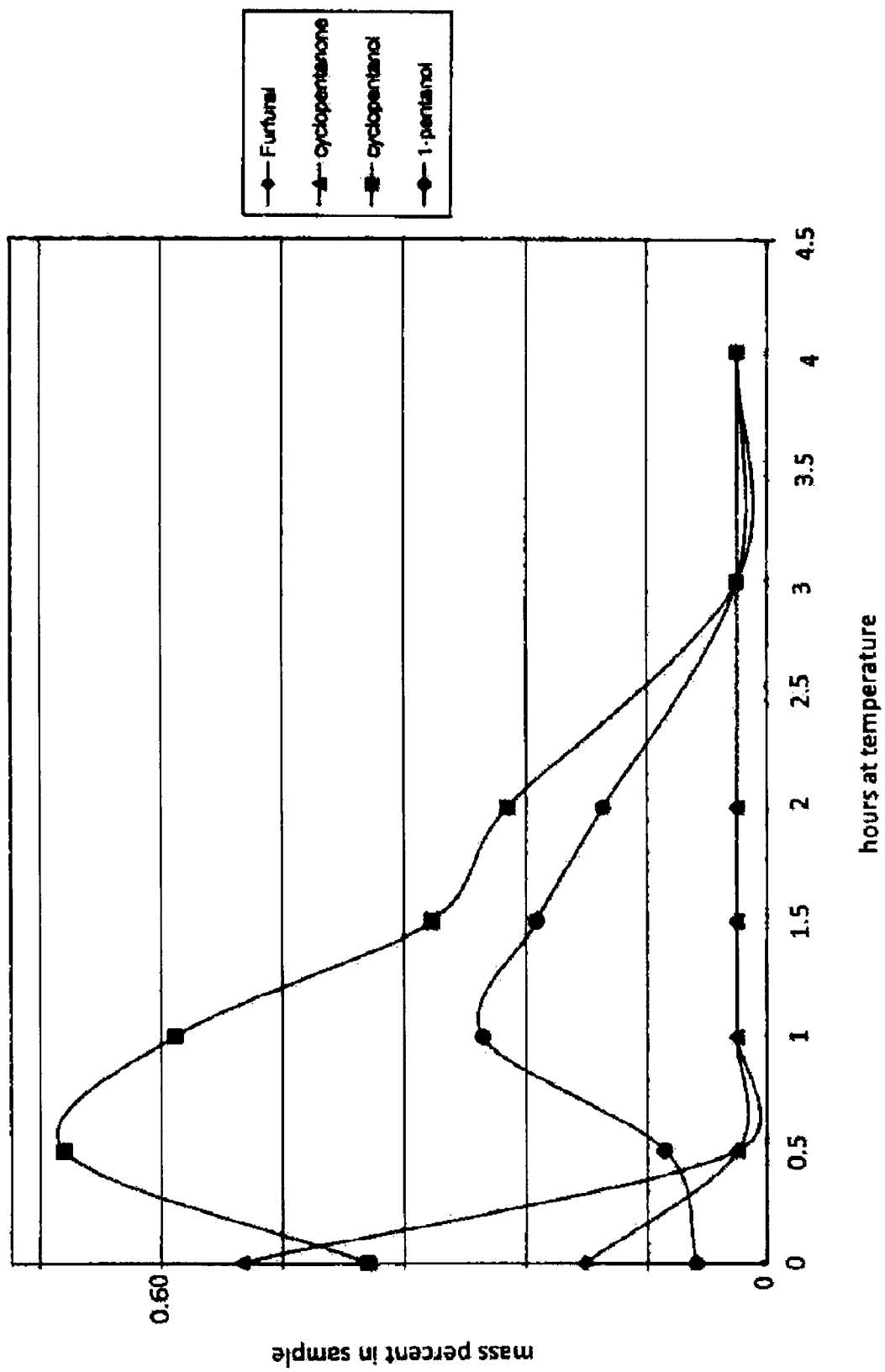

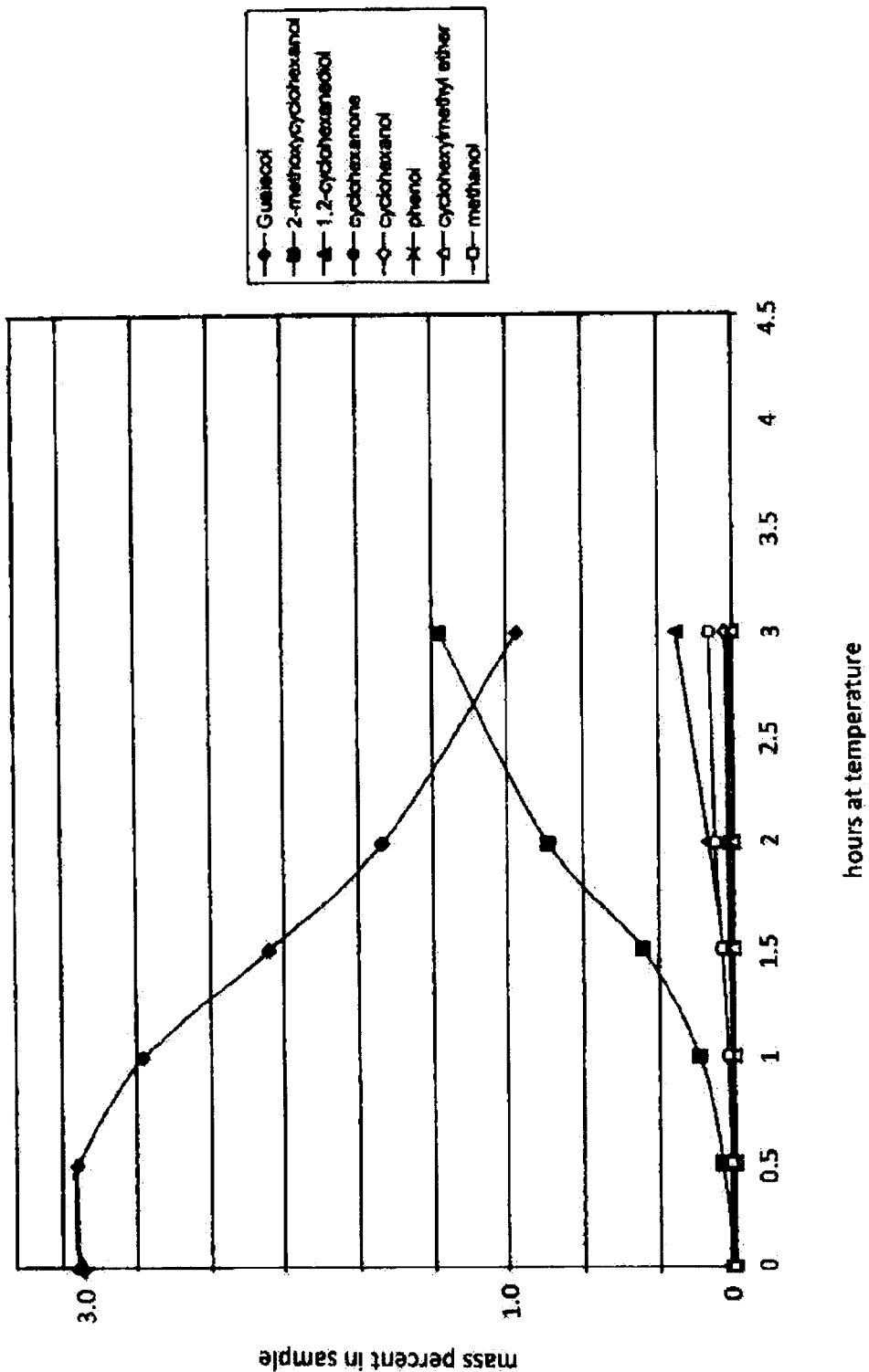

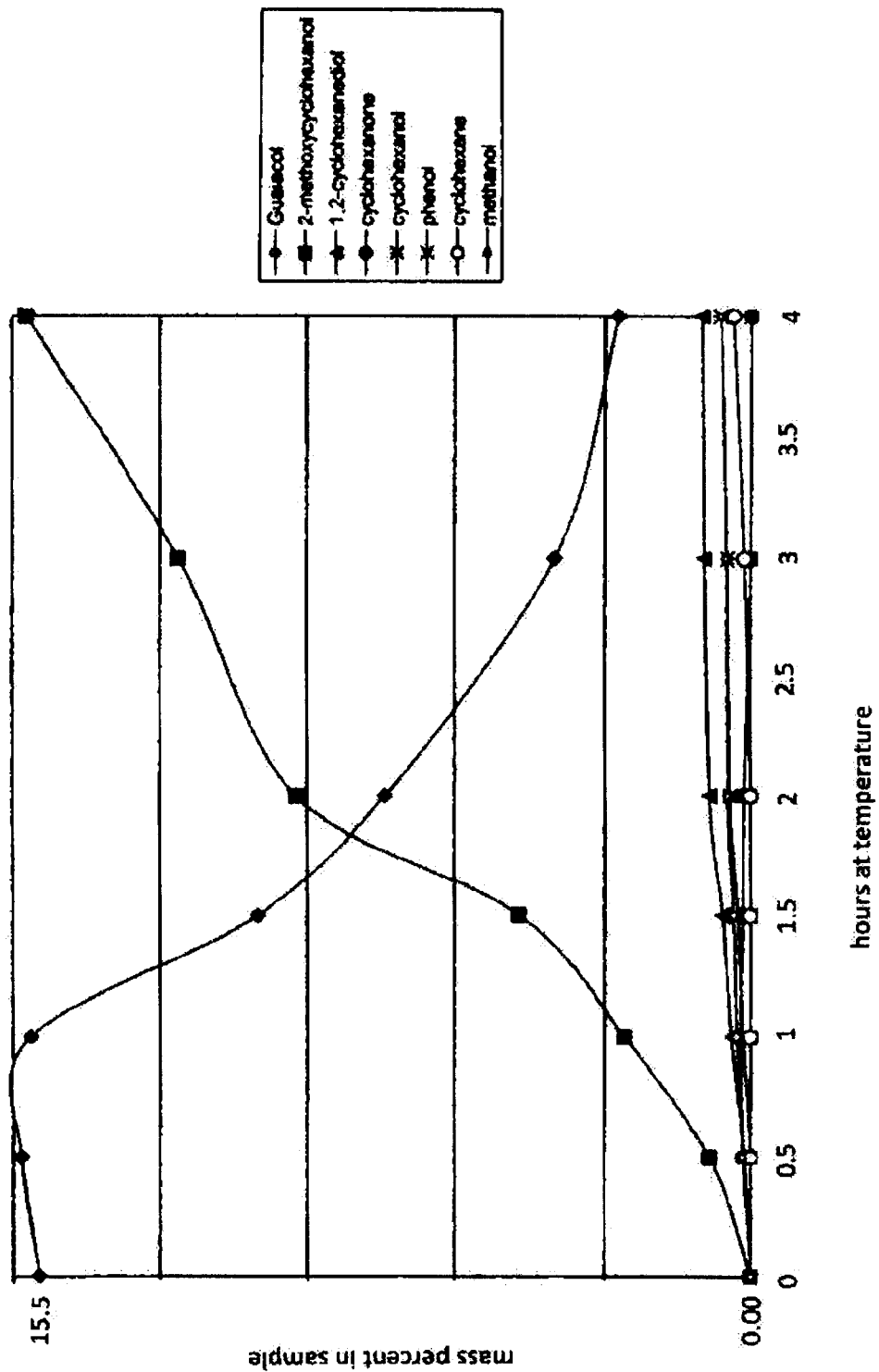

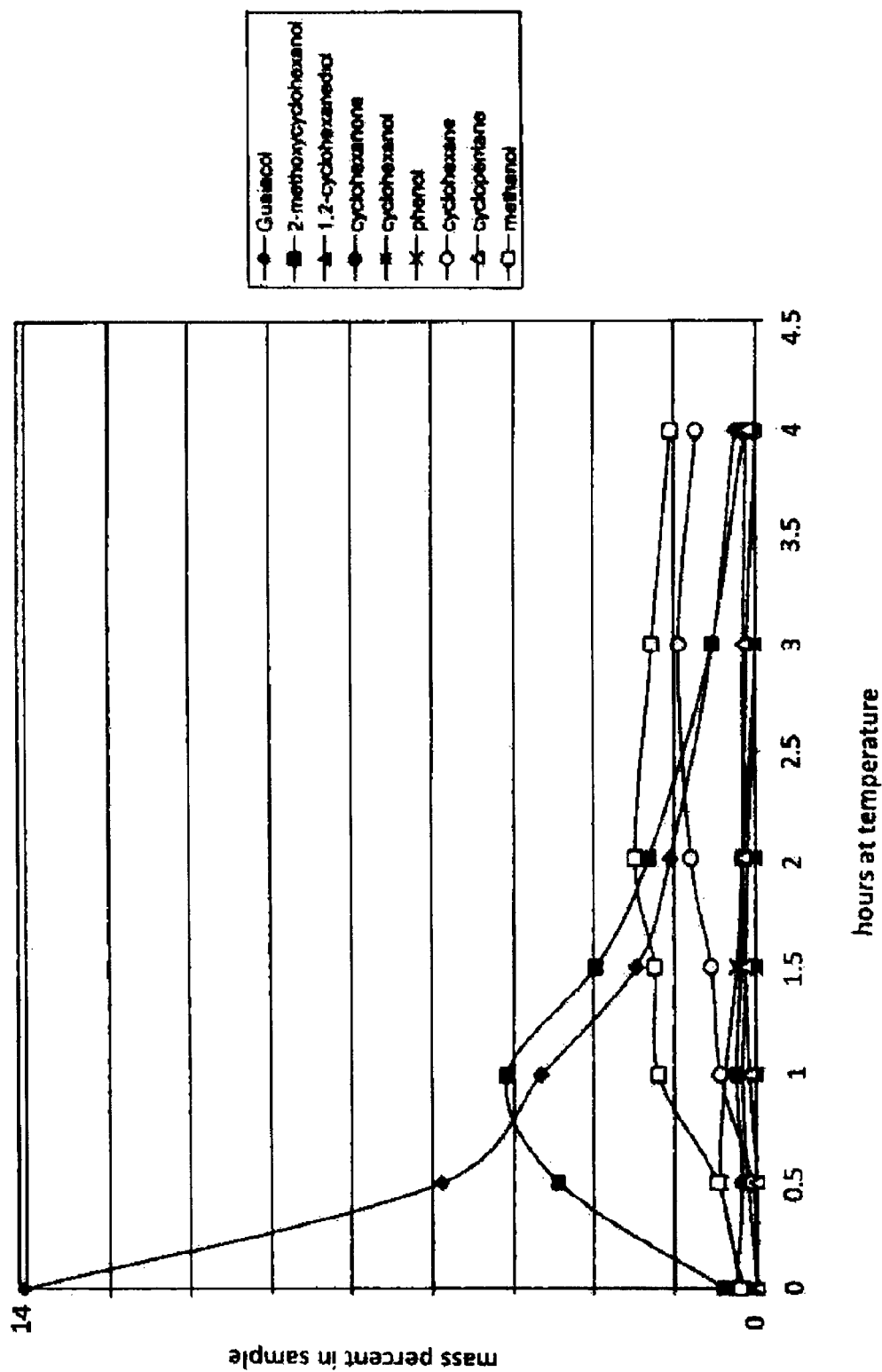
Figure 15. Guaiacol Hydrogenation/Pd-300C

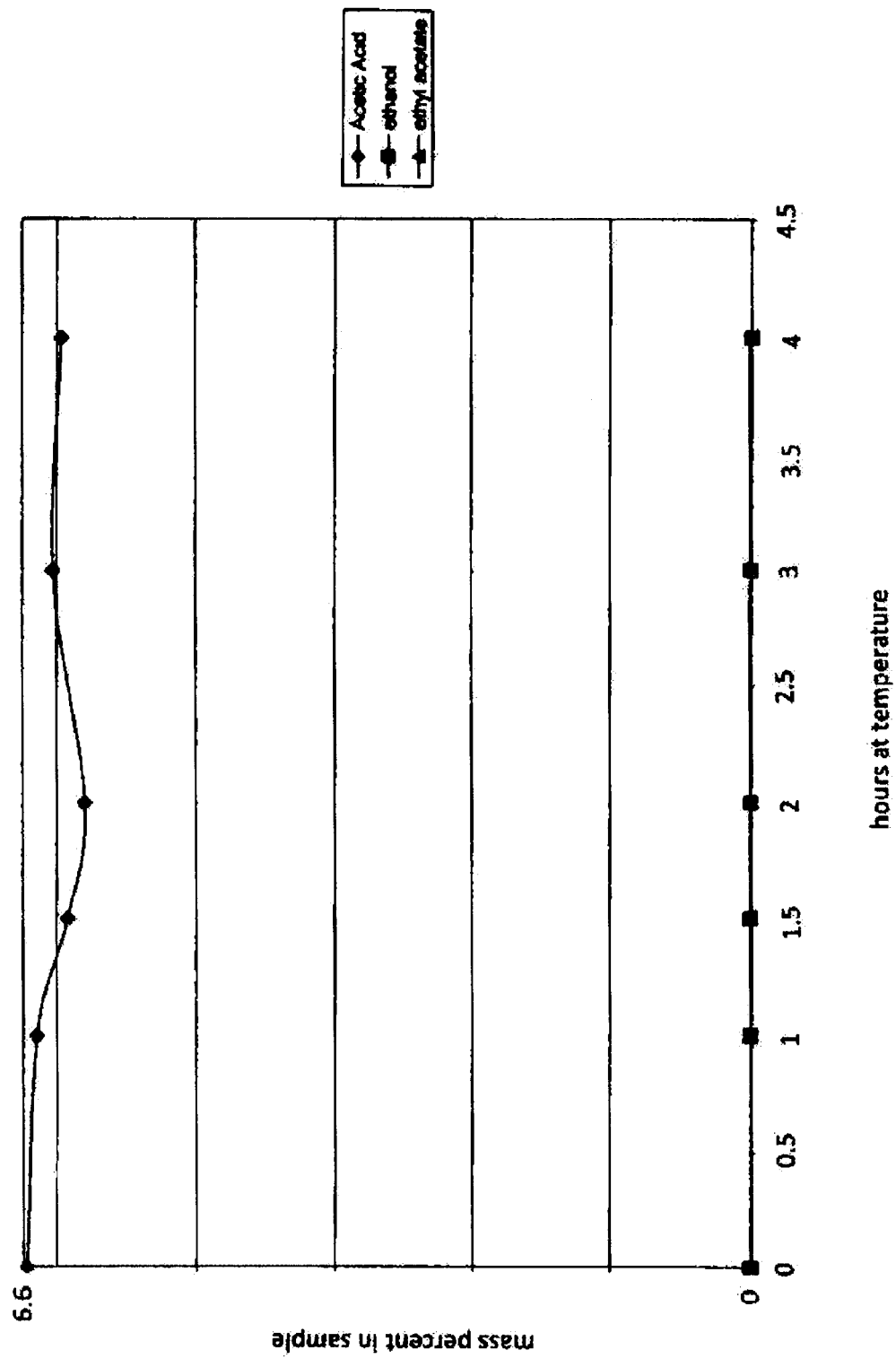

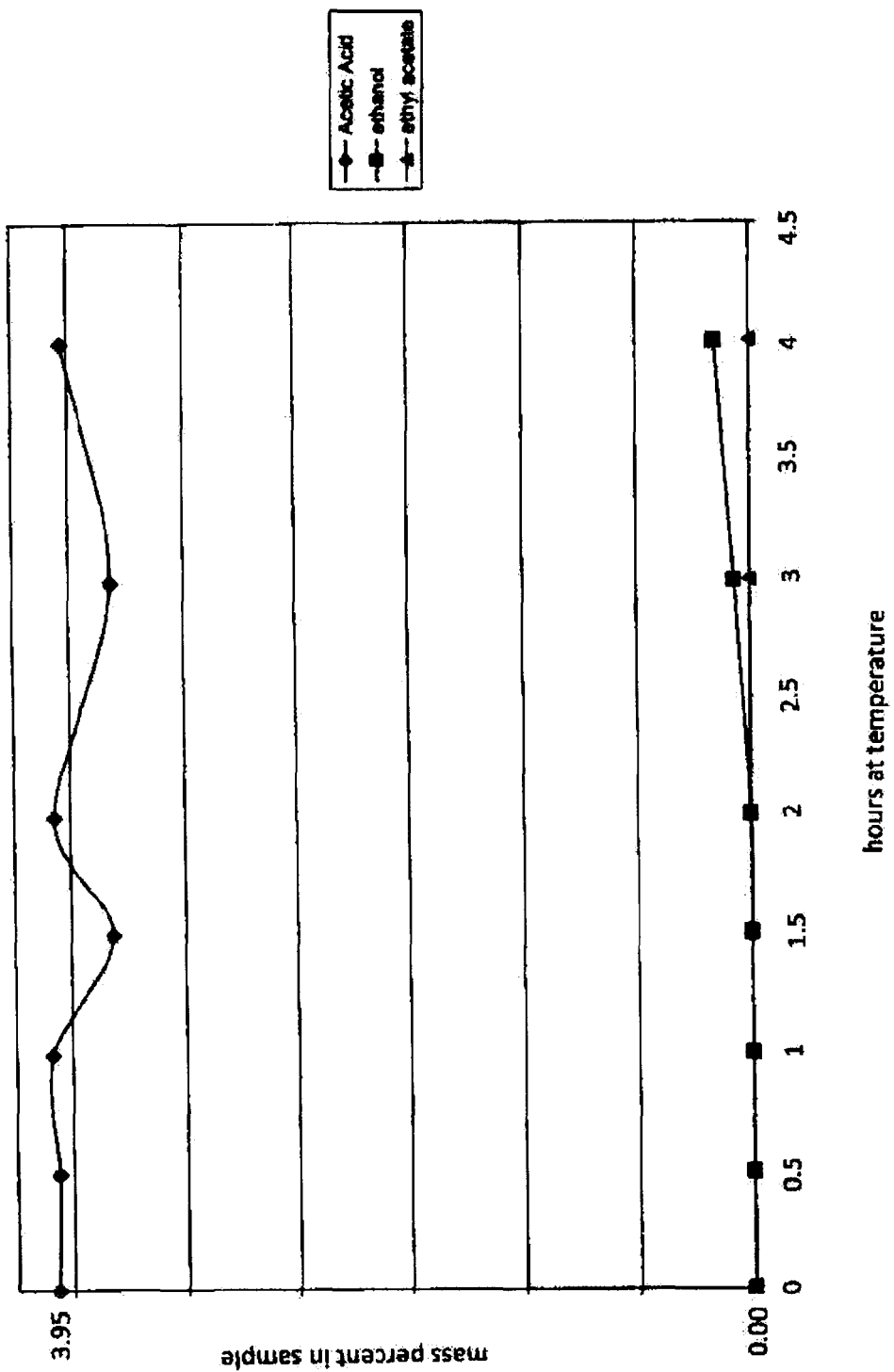

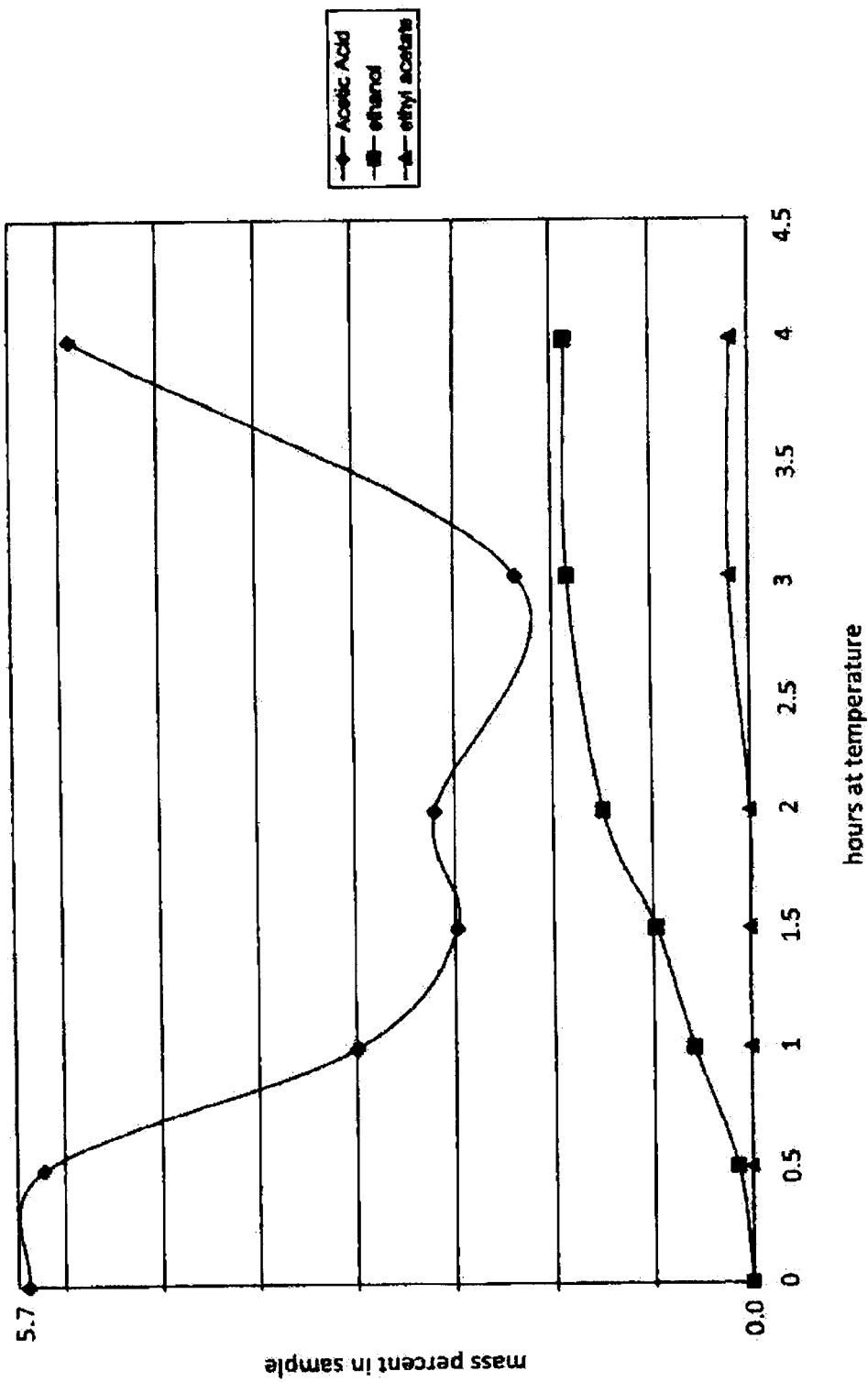
Figure 18. Acetic Acid Hydrogenation/Pd-300C

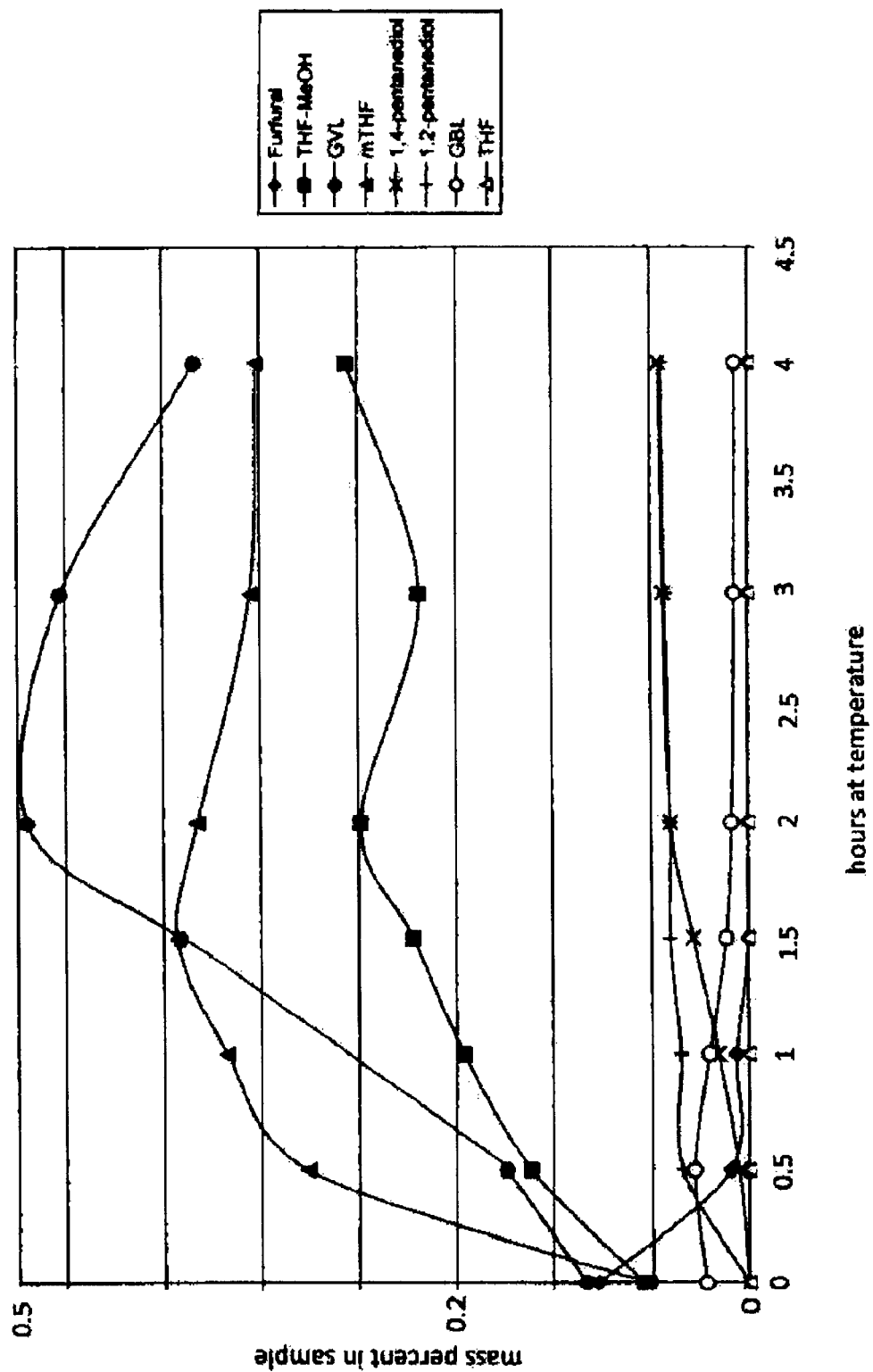
Figure 19. Furfural Hydrogenation to Cyclic Ethers/Pd-200C

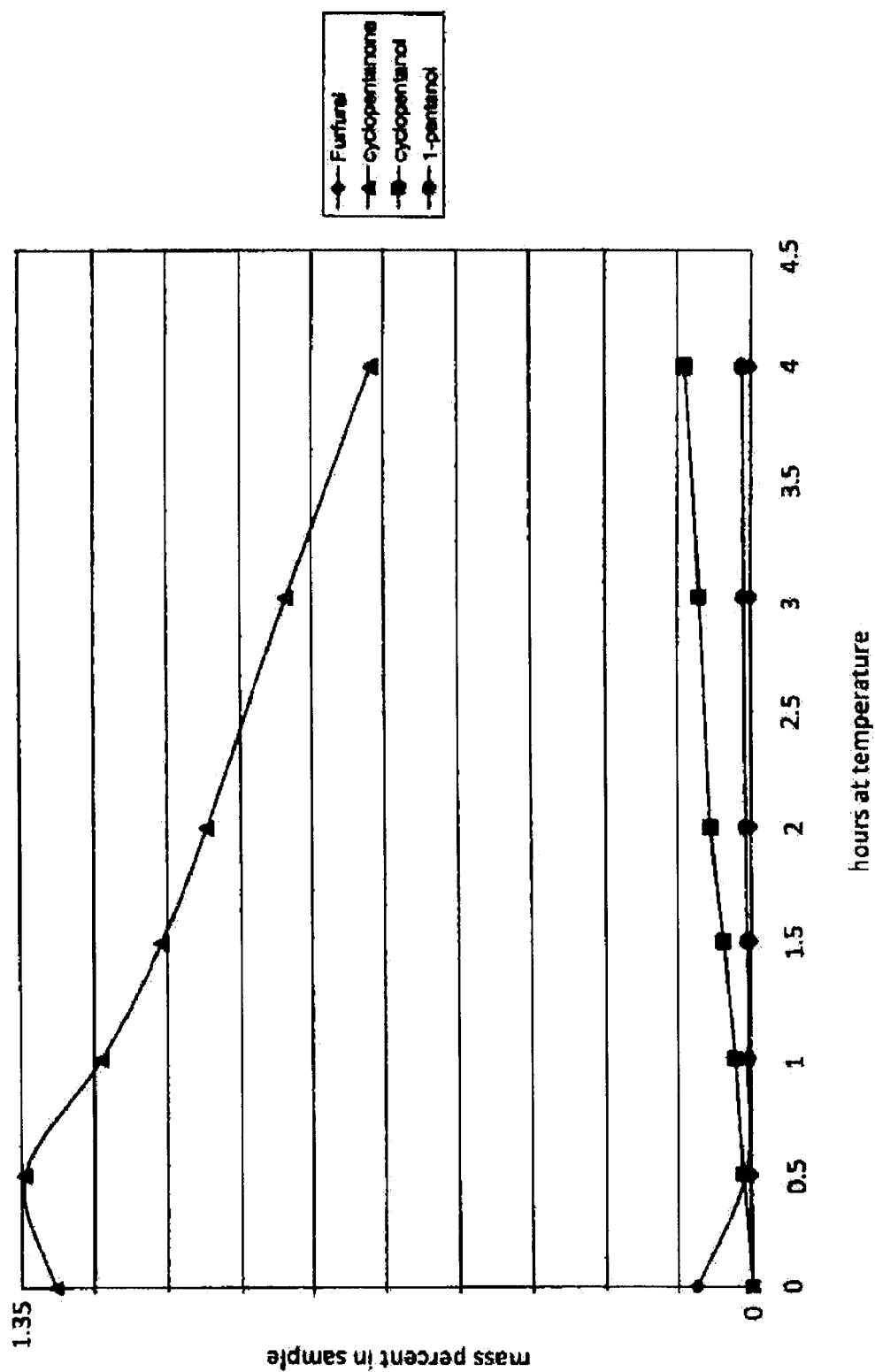
Figure 20. Furfural Hydrogenation to Alcohols/Pd-200C

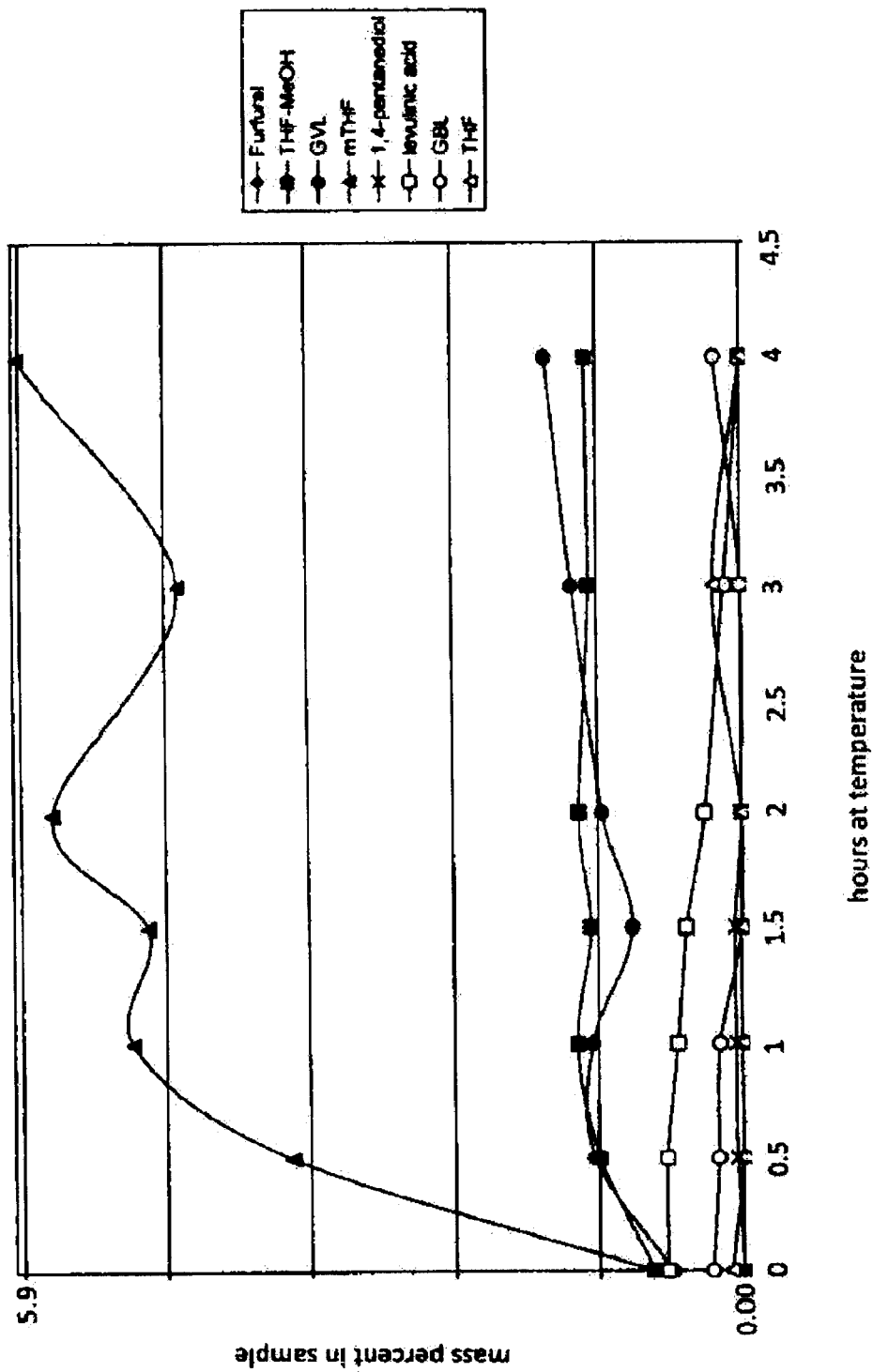
Figure 21. Furfural Hydrogenation to Cyclic Ethers/Pd-250C

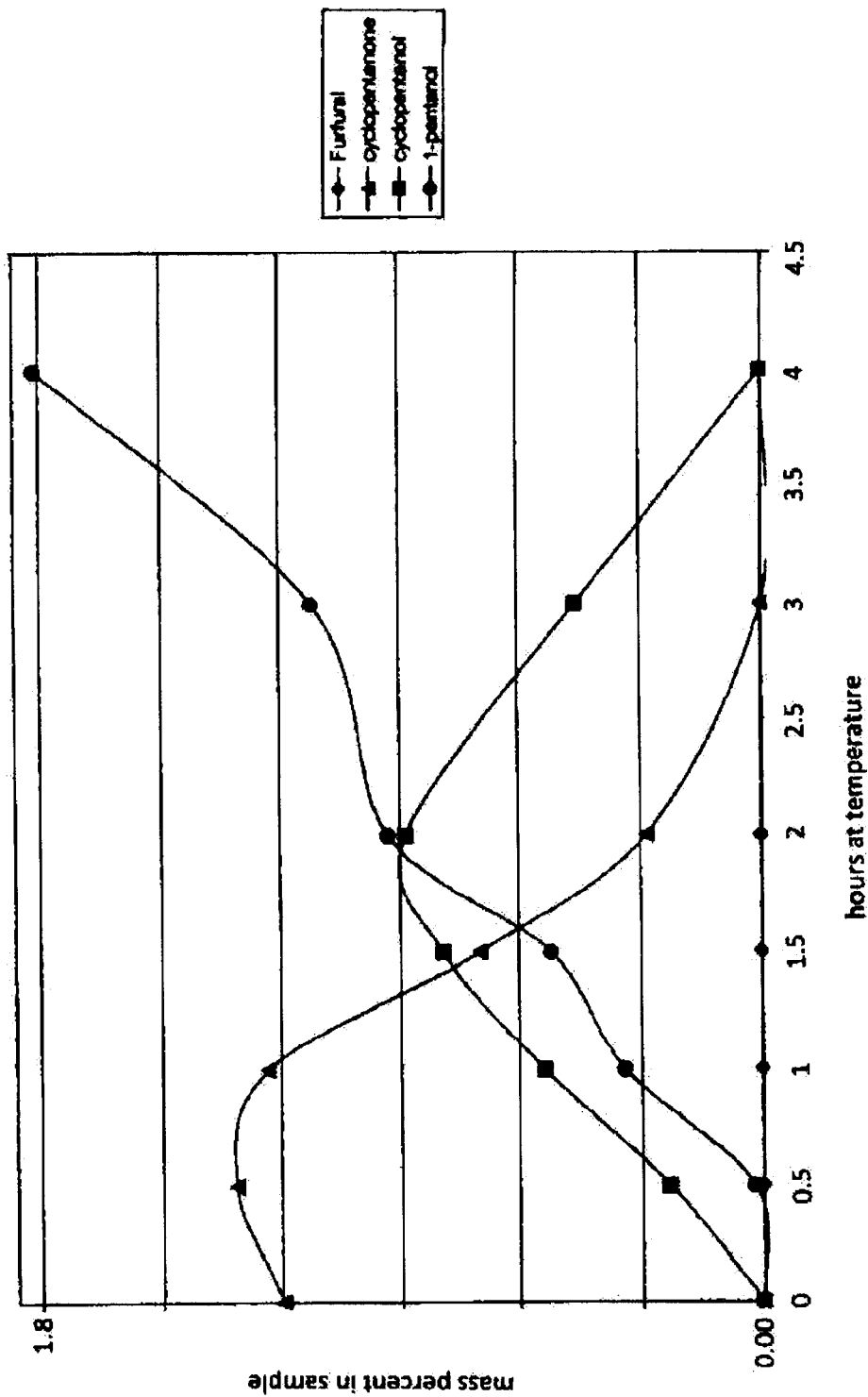

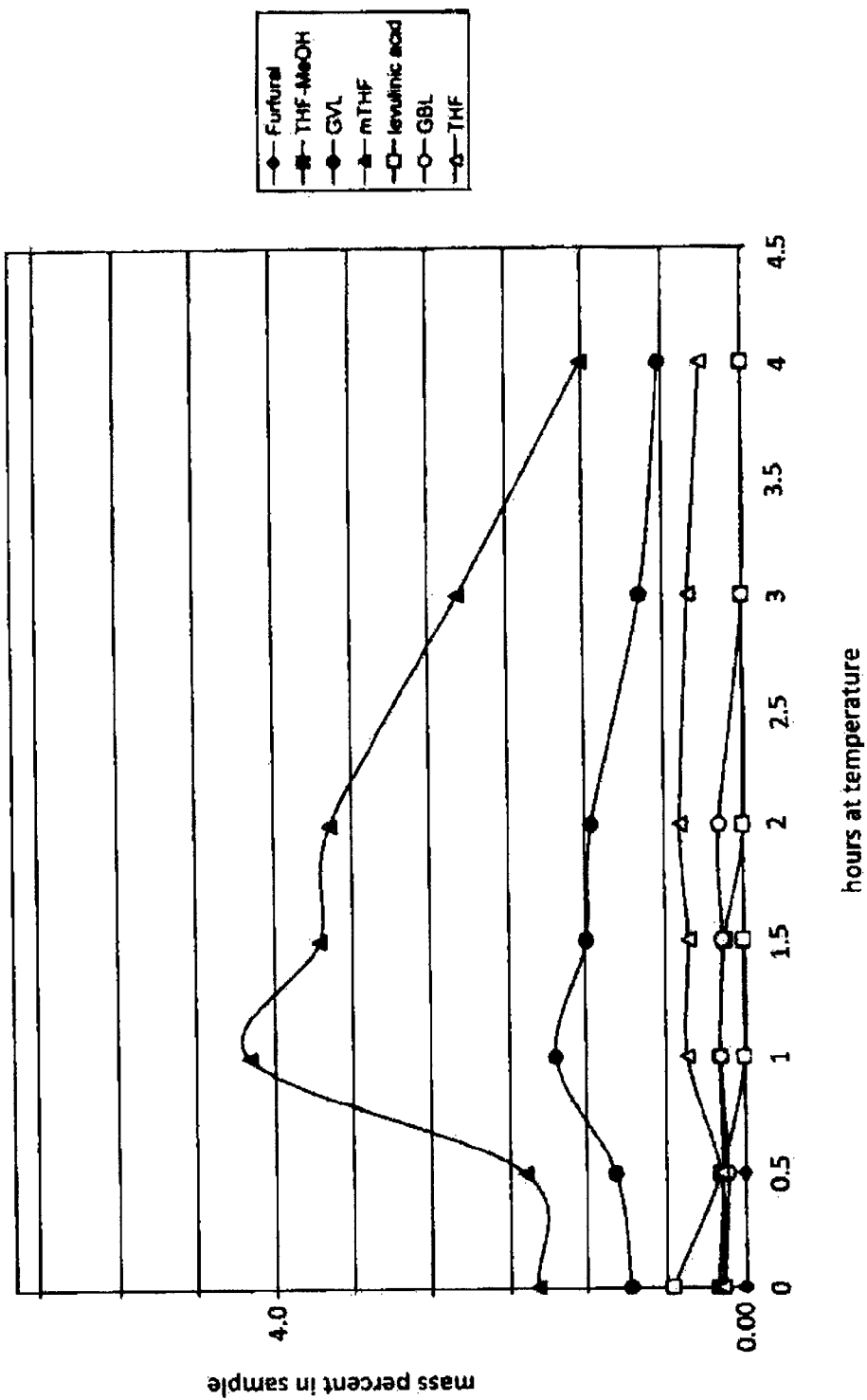

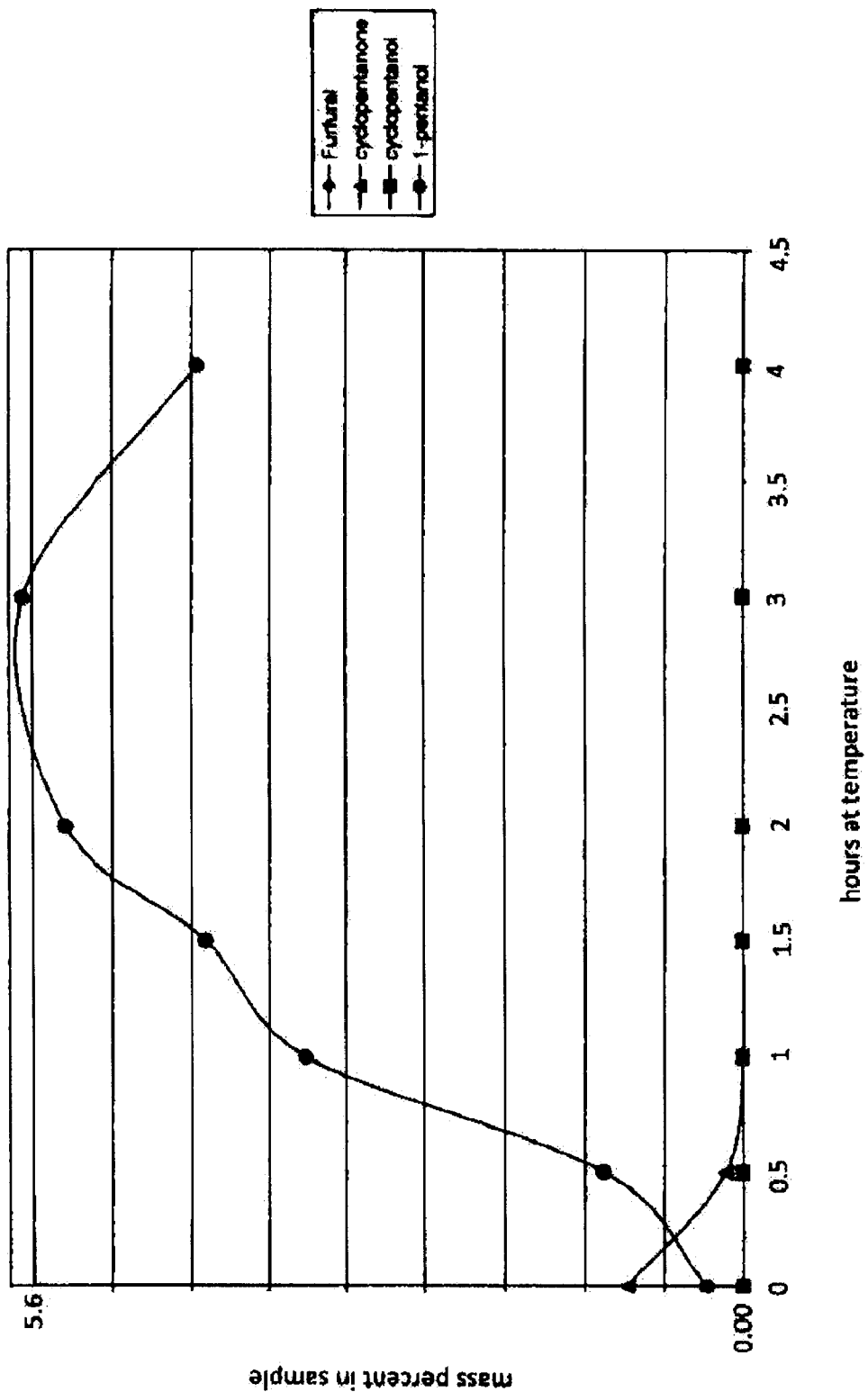
Figure 24. Furfural Hydrogenation to Alcohols/Pd-300C

PALLADIUM CATALYZED HYDROGENATION OF BIO-OILS AND ORGANIC COMPOUNDS

RELATED APPLICATIONS

This application is a continuation of U.S. patent application Ser. No. 11/759,075, filed Jun. 6, 2007 now U.S. Pat. No. 7,425,657.

GOVERNMENT RIGHTS

This invention was made with Government support under Contract DE-AC0676RL01830 awarded by the U.S. Department of Energy. The Government has certain rights in the invention.

FIELD OF THE INVENTION

The invention relates to methods of hydrodeoxygenation of bio-oils.

INTRODUCTION

Early work on the catalytic hydroprocessing of bio-oil (product liquids from fast pyrolysis of biomass) focused on fuel production, with initial studies aimed at complete hydrodeoxygenation (HDO) to produce fuels compatible with existing petroleum products. Subsequent work involved the development of low-severity hydrogenation to produce a more thermally stable, but not entirely deoxygenated, fuel. These efforts produced useful information relative to the thermal stability of bio-oil in processing systems, the limitations in high-temperature processing of bio-oil, and the requirements for producing fuels from bio-oil by catalytic hydrogenation.

The early HDO results showed that the process operated in conventional petroleum hydrotreaters needed to be modified for bio-oil[i]. For example, a low-temperature stabilization step was required before finishing the HDO at conventional higher temperature[ii]. Without the low-temperature step, direct high-temperature catalytic processing resulted in high levels of char/coke production that plugged the catalyst bed without production of liquid hydrocarbon fuels. It was concluded that the thermal instability of the bio-oil, as produced in fast pyrolysis, led to decomposition and polymerization more rapidly than the catalytic hydrogenation could cause the conversion to light hydrocarbon liquid fuels. Also, while conventional alumina supported cobalt-molybdenum and nickel-molybedenum catalysts were useful for HDO in the sulfided form[iii,iv], i.e., high yields of hydrocarbon oil product could be produced without fully saturating the aromatic rings, the instability of the alumina supports in the presence of the high levels of water was recognized as a shortcoming[v]. In addition, a high level of coking was identified, and carbon supports were evaluated as a replacement for alumina[vi].

[i] Elliott, D. C., & Baker, E. G. (1987) Hydrotreating biomass liquids to produce hydrocarbon fuels, In: Energy from Biomass and Waste X. (Ed. D. L. Klass), pp. 765-784. Institute of Gas Technology, Chicago.
[ii] Elliott, D. C., & Baker, E. G. (1989) Process for upgrading biomass pyrolyzates. U.S. Pat. No. 4,795,841.
[iii] Baker, E. G., & Elliott, D. C. (1988) Catalytic upgrading of biomass pyrolysis oils, In: Research in Thermochemical Biomass Conversion, (Eds. A. V. Bridgwater & J. L. Kuester), pp. 883-895, Elsevier Applied Science, London.
[iv] Baldauf, W., & Balfanz, U. (1992) Upgrading of Pyrolysis Oils from Biomass in Existing Refinery Structures, VEBA OEL AG, Gelsenkirchen. Final Report JOUB-0015.
[v] Laurent, E.; (1993) Etude et contrôle des réactions d'hydrodésoxygénation lors de l'hydroraffinage des huiles de pyrolyse de la biomasse. D.Sci. thesis, Universite Catholique de Louvain, Louvain-1a-Neuve, Belgium.
[vi] Centeno, A.; David, A.; Vanbellinghen, Ch.; Maggi, R.; Delmon, B.; (1997) Behavior of catalysts supported on carbon in hydrodeoxygenation reactions, In: Developments in Thermochemical Biomass Conversion, (Eds. A. V. Bridgwater & D. G. B. Boocock), pp. 589-601, Blackie Academic and Scientific, London.

Experimental results from hydrotreating bio-oil in the presence of metallic catalysts have been reported. Some batch reactor results with palladium, copper chromite and nickel catalysts have been reported[vii,viii]. In those tests, operation at 20° C. caused slight changes, while tests at 100° C. resulted in what were described as "drastic changes." Various ketones were reacted, but acetic acid was not reduced. Although gas chromatographic separations were performed on the products, detailed chemical conversion conclusions were not reported.

[vii] Meier, D.; Wehlte, S.; Wulzinger, P.; Faix, O. (1996) Upgrading of Bio-oils and flash pyrolysis of CCB-treated wood waste. In: Bio-Oil Production and Utilization, (Eds. A. V. Bridgwater & E. N. Hogan), pp. 102-112, CPL Scientific Ltd, Newbury, UK.
[viii] Meier, D.; Bridgwater, A. V.; DiBlasi, C.; Prins, W. (1997) Integrated chemicals and fuels recovery from pyrolysis liquids generated by ablative pyrolysis. In: Biomass Gasification and Pyrolysis: State of the Art and Future Prospects, (Eds. M. Kaltschmitt & A. V. Bridgwater), pp. 516-527, CPL Scientific Ltd, Newbury, UK.

Hydrogenation of fast pyrolysis oil was also studied by Scholze[ix] using a batch reactor with various metal catalysts and without catalyst at low temperatures. She concluded that reaction temperatures above 80° C. are unsuitable for hydrogenation of bio-oils because the product phases separate. Further, none of the combinations of bio-oils, catalysts, and conditions, which were tested, resulted in a more stable oil. She found that palladium was essentially inactive at 60° C. Raney nickel at 80° C. resulted in reduced viscosity over time (without phase separation), while copper chromite at the same temperature resulted in a slightly more viscous oil over time. Nickel metal was tested at temperatures from 22° C. to 100° C. At 22° C. there was noticeable reduction in carbonyl (~15%) without noticeable change in physical properties. At 82° C. and 100° C. the product oil separated into two phases (as did the copper chromite catalyzed product). Chemical analysis of these products was performed to a limited degree, but little was concluded about the changes in the oil composition. Carbonyl analysis showed no change in the palladium catalyzed tests and up to a 20% reduction at the intermediate temperatures of 50° C. with nickel metal catalyst. Although gas chromatographic separations were performed on the products, detailed chemical conversion conclusions were not reported.

[ix] Scholze, B. (2002) Long-term stability, catalytic upgrading, and application of pyrolysis oils—Improving the properties of a potential substitute for fossil fuels. doctoral dissertation, University of Hamburg, Hamburg, Germany.

Our earlier results with the ruthenium catalyst also included some model compound studies[x]. In that work, the conversion of substituted guaiacols (4-alkyl-2-methoxyphenols) through substituted methoxycyclohexanols to substituted cyclohexanediols at low temperature and substituted cyclohexanols at higher temperature was identified. Both acetol (1-hydroxy-2-propanone), and 3-methyl-4-cyclopenten-1-one were readily hydrogenated to propylene glycol and methylcyclopentanol, respectively. The furfural was hydrogenated through several steps to the stable form as tetrahydrofuran-methanol, with only minor evidence of further hydrogenation.

[x] Elliott, D. C.; Neuenschwander, G. G.; Hart, T. R.; Hu, J.; Solana, A. E.; Cao, C. "Hydrogenation of bio-oil for chemical and fuel production." In: Proceedings of Science in Thermal and Chemical Biomass Conversion Conference, Victoria, BC CANADA, August 30-Sep. 4, 2004.

SUMMARY OF THE INVENTION

The invention provides a method of hydrodeoxygenation of bio-oil, comprising: providing a bio-oil and hydrogen (H2); and reacting the bio-oil and hydrogen over a catalyst at a temperature of more than 200° C. The catalyst comprises Pd. In this method, an oil, which is a liquid at room temperature, is produced from the reaction of the bio-oil and hydrogen. The term "liquid oil" means an oil that is a liquid at room temperature.

Typically, this method is conducted in presence of water; the bio-oil typically comprises 5 to 50 mass % water. The bio-oil can be a single phase or multiphase liquid. In preferred embodiments, water is removed during the step of reacting the bio-oil and hydrogen over a catalyst. Preferably, the method is characterized by a bio-oil deoxygenation of at least 50% and/or a yield of liquid oil of at least 60%. In preferred embodiments, the bio-oil comprises acetic acid and at least 30% of the acetic acid in the bio-oil is converted to ethanol.

The invention also includes product mixtures made from the inventive methods.

In a further aspect, the invention provides a method of hydrogenating furfural, guaiacol or a substituted guaiacol, comprising: providing a liquid comprising furfural, guaiacol or a substituted guaiacol; providing hydrogen (H2); and reacting the furfural, guaiacol or a substituted guaiacol with hydrogen over a catalyst at a temperature of more than 200° C. The catalyst comprises Pd. In this method, the furfural, guaiacol or substituted guaiacol is converted to a hydrogenated product. The furfural, guaiacol or a substituted guaiacol can be present in a bio-oil or in any other composition.

In some embodiments of hydrogenating furfural, the method is carried out at a temperature of at least 280° C., and at least 5% of the furfural is converted to 1-pentanol. In some embodiments, at least 6% of the furfural is converted to 2-methyl-tetrahydrofuran; preferably at a temperature of about 250 to about 300° C.

BRIEF DESCRIPTION OF THE FIGURES

FIG. 1 Guaiacol Hydrogenation over Ruthenium at 150 C
FIG. 2 Guaiacol Hydrogenation over Ruthenium at 200 C
FIG. 3 Guaiacol Hydrogenation over Ruthenium at 250 C
FIG. 4 Acetic Acid Hydrogenation over Ruthenium at 150 C
FIG. 5 Acetic Acid Hydrogenation over Ruthenium at 200 C
FIG. 6 Acetic Acid Hydrogenation over Ruthenium at 250 C
FIG. 7 Cyclic Ether Products from Furfural Conversion over Ruthenium at 150 C
FIG. 8 Cyclic Ketone Products from Furfural Conversion over Ruthenium at 150 C
FIG. 9 Cyclic Ether Products from Furfural Conversion over Ruthenium at 200 C
FIG. 10 Cyclic Ketone Products from Furfural Conversion over Ruthenium at 200 C
FIG. 11 Cyclic Ether Products from Furfural Conversion over Ruthenium at 250 C
FIG. 12 Cyclic Ketone Products from Furfural Conversion over Ruthenium at 250 C
FIG. 13 Guaiacol Hydrogenation over Palladium at 200 C
FIG. 14 Guaiacol Hydrogenation over Palladium at 250 C
FIG. 15 Guaiacol Hydrogenation over Palladium at 300 C
FIG. 16 Acetic Acid Conversion over Palladium at 200 C
FIG. 17 Acetic Acid Conversion over Palladium at 250 C
FIG. 18 Acetic Acid Conversion over Palladium at 300 C
FIG. 19 Cyclic Ether Products from Furfural Conversion over Palladium at 200 C
FIG. 20 cyclic Ketone Products from Furfural Conversion over Palladium at 200 C
FIG. 21 Cyclic Ether Products from Furfural Conversion over Palladium at 250 C
FIG. 22 Cyclic Ketone Products from Furfural Conversion over Palladium at 250 C
FIG. 23 Cyclic Ether Products from Furfural Conversion over Palladium at 300 C
FIG. 24 Cyclic Ketone Products from Furfural Conversion over Palladium at 300 C

DETAILED DESCRIPTION OF THE INVENTION

Bio-oil (product liquids from fast pyrolysis of biomass) is a complex mixture of compounds derived from the thermal breakdown of the bio-polymers in biomass. In the case of lignocellulosic biomass, the structures of three major components, cellulose, hemicellulose and lignin, are well represented by the bio-oil components. In order to study the chemical mechanisms of catalytic hydroprocessing of bio-oil, three model compounds were chosen to represent those components. A large number of mono- and di-methoxy phenols are typically found in bio-oil derived from softwood or hardwood, respectively. Guaiacol was used to represent the mono- and di-methoxy phenols found in bio-oil. A major pyrolysis product group from cellulosics includes furfural and similar compounds. Acetic acid is a major product from biomass pyrolysis, which has important impacts on the further processing of the bio-oil because of its acidic character. These three compounds were processed using palladium or ruthenium catalyst over a temperature range from 150° C. to 350° C. The batch reactor was sampled during each test over a period of four hours. The samples were analyzed by gas chromatography with both a mass selective detector and a flame ionization detector. The products were determined and the reaction pathways for their formation are suggested based on these results. Both temperature and catalyst metal have significant effects on the product composition.

Catalyst

The catalyst in the inventive methods should contain sufficient palladium to sustain a significant level of activity under the selected reaction conditions. Preferably the catalyst contains at least 0.1% Pd (throughout this description, % indicates weight % unless otherwise specified, with weight % Pd is calculated based on the weight of a wall coating or catalyst pellet or other configuration that includes the weight of catalyst support but not the weight of the chemical reactor itself. More preferably, the catalyst comprises at least 1 weight % Pd, and in some embodiments the catalyst comprises 2 to 5 weight % Pd. In addition to Pd, other metals may be present. In preferred embodiments, the catalyst metal consists essentially of Pd (without other metals that substantially affect the process), or consists of Pd (without other metals). Pd metal has been found to be stable in this processing environment despite the relatively high level of water and oxygenated materials.

Preferably, Pd metal particles are dispersed on a support. The supports should be stable to the reaction conditions. Preferred supports are carbon, titania (preferably rutile), and zirconia (preferably the monoclinic form). Activated carbon is a well-known high-surface area (typically ~1000 m²/g) support material which has been shown to be stable in hot water processing environments; rutile titania and monoclinic zirconia have lesser surface area (typically 30-80 m²/g) and have demonstrated utility for catalytic metal support and use in the hot water processing environment (see U.S. Pat. Nos. 5,616,154; 6,235,797 incorporated herein as if reproduced in full below).

Reactants

Bio-oils are a complex mixture of compounds, including oxygenates, that are obtained from the breakdown of bio-polymers. Bio-oils can be derived from plants such as grasses and trees, and other sources of ligno-cellulosic material, such as derived from municipal waste, food processing wastes, forestry wastes and pulp and paper byproducts. Starting materials of the present invention typically include water, typically at least 5 mass % water in a liquid, in some embodiments at least 10% or at least 20% water. In some embodiments there is 5 to 50 mass % water, in some embodiments 10 to 40 mass %. In some embodiments up to 35%. The water may be present in a single phase with the oil, or primarily in a second phase (for an example an emulsion with the aqueous phase as either the major or minor component), or in mixture of phases. In some preferred embodiments, a second (primarily) water phase is formed during a hydrogenation reaction and is removed during or after the hydrogenation treatment.

Hydrogen can be added separately or together with the bio-oil into a reactor. In the case of a continuous process, hydrogen can be added along the length of a reactor. The hydrogen is preferably added in excess of stoichiometry to maximize reaction rate by minimizing mass transfer limitations. In our testing, typical hydrogen feed to the reactor is 10,000 standard cubic feet (SCF) of hydrogen per barrel (bbl) of oil feed (1781 liter/liter) and overall testing from 5500 to 18300 SCF/bbl.

Preferably, hydrogen is reacted with the bio-oil feedstock at a level of at least 50 liter/liter, more preferably at least 100 liter/liter, and still more preferably at least 200 liter/liter, in some embodiments in the range of 100 to 300 liter/liter, and in some embodiments in the range of 100 to 175 liter/liter. Excess hydrogen may be recycled into a reactor.

Reactor Configuration

Apparatus for conducting the inventive processes is not limited. The processes can be conducted batchwise or continuously. The catalyst can be present as a wall coating, fluidized bed, fixed bed of particles or pellets, etc. A fixed bed of catalyst particles has the advantage of ease of design and operation (clean-up and catalyst replacement). In some embodiments, fluidized bed reactors may be preferred, especially if the bio-oil is contaminated with inorganic material. In some embodiments, wall coated reactors, which have certain advantages for heat and mass transfer, may be preferred.

Operating Conditions

The inventive processes are carried out at temperatures greater than 200° C., more preferably in the range of 220 to 500° C., in some embodiments at least about 250° C. or at least about 300° C.; in some embodiments in the range of 240° C. or about 250° C. to 450° C., or 400° C., or 350° C., or about 300° C.

The reactions are carried out under pressure. Preferably, the processes are carried out at pressures of at least 1 MPa, more preferably at least 5 MPa, in some embodiments at least 10 MPa, in some embodiments pressure is in the range of 1 MPa to 25 MPa.

Preferably, bio-oils are not preheated prior to the hydrogenation since prolonged heating or storage at elevated temperatures can cause degradation. Similarly, in preferred embodiments the products are quickly cooled after hydrogenation.

For continuous processing, the process desirably has as high a liquid hourly space velocity (LHSV) as possible. LHSV is based on the liquid volume of feedstock (including water) at standard temperature and pressure that is fed into a reactor. The reactor volume used for calculating LHSV is the volume where catalyst is present (in the case of a wall coating, it includes the volume of the flow path past the catalyst wall coating). LHSV (in volume per volume per hour) is preferably at least 0.01, more preferably at least 0.1, and in some embodiments about 0.05 to about 0.25.

In view of the descriptions herein, for any given bio-oil (including bio-oil derived) feedstock, conditions can be controlled to produce a set level of reactant conversion and/or product yield. The inventive methods can be defined to include any of the conversions and/or yields from the Examples. Due to the complexity of bio-oils, this can be the best way (indeed the only way) to define certain aspects of the invention. For example, the product is preferably at least 40% deoxygenated, more preferably at least 50% deoxygenated, and in some embodiments is about 50% to about 65% deoxygenated. "Deoxygenation" is measured on a dry basis (excluding water) and is based on the reduction of the mass % of oxygen in the oil. The yield of oil (defined on a dry basis, excluding water) is preferably at least 60%, more preferably 75%, and in some embodiments is up to about 83%. The yield and % deoxygenation are properties of the inventive methods. The term "oil" is defined to mean a substance that is a liquid at room temperature and does not include water (although water is sometimes dissolved or suspended with oil).

Guaiacol is 2-methoxy-phenol. Substituted guaiacols are 2-methoxy-phenol with alkyl substituents (having up to 6 carbons), such as propyl, methyl, and ethyl, in the 4-position. In some preferred embodiments of the invention, at least about 50% (in some embodiments at least about 60%) of guaiacol in a starting feedstock is converted to 2-methoxycyclohexanol, or at least about 50% (in some embodiments at least about 60%) of substituted guaiacol in a starting feedstock are converted to cyclohexanol derivatives (compounds that include a cyclohexanol moiety). In some embodiments, about 50% to about 80% of guaiacol and/or substituted guaiacols are converted to 2-methoxy-phenol or other cyclohexanol derivatives. In a preferred embodiment, this reaction takes place at a temperature of at least about 250° C., in some embodiments in the range of about 240° C. to about 270° C.

In some preferred embodiments, at least about 50% of acetic acid in a feedstock is consumed in a hydrogenation treatment; in some embodiments about 50% to about 65% is consumed. In some preferred embodiments, at least about 30% of acetic acid is converted to ethanol, in some embodiments about 30% to about 40% of acetic acid is converted to ethanol.

Preferably, at least 90%, more preferably at least 99% of furfural is consumed in the hydrogenation treatment. In some preferred embodiments, at least about 5% of the furfural is converted to 1-pentanol, in some embodiments about 5% to about 9% of furfural is converted to 1-pentanol; preferably at temperatures of at least about 280° C., in some embodiments about 280° C. to about 350° C. In some preferred embodiments, at least about 6% of the furfural is converted to 2-methyl-tetrahydrofuran (mTHF), in some embodiments about 6% to about 10% of furfural is converted to m-thf; preferably at temperatures of at least about 250° C., in some embodiments about 250° C. to about 300° C.

To test conversion percentages in processing a bio-oil, a small amount of labeled compound can be injected into a feed stream and the product stream can be analyzed for labeled compounds.

Products

The invention also includes product mixtures, especially product mixtures that are produced by the processes of the invention. The invention includes fuels made by the inventive processes. Products mixtures made by the inventive processes are unique mixtures that have one or more advantageous properties such as desirable combustion properties and high proportions of desirable chemical products such as ethanol and/or 2-methylcyclohexanol.

The products resulting from the hydrogenation treatment can be used without further treatment. More preferably, the product resulting from the hydrogenation treatment is further treated by additional processes such as: water removal, separation of one or more chemical components, and additional hydrogenation or other fuel processing treatment.

Results of Testing—Catalysts and Conditions

As described in the examples, three chemical models were reacted at 150, 200, 250, and 300° C. using either the palladium or the ruthenium catalyst. The products varied with temperature and the catalyst metal. The experimental product from the catalyzed tests contained about 30 components of sufficient concentration to be identified and quantified. This level of complexity can be compared to whole hydrogenated bio-oil, which typically contains hundreds of components. The components were separated into four groups to represent the products from acetic acid, guaiacol and two collections of products from furfural.

Ruthenium Catalyzed Hydrogenations. For guaiacol hydrogenation in the presence of ruthenium catalyst the products were similar to those identified earlier in our laboratory. At 150° C., 54% of the guaiacol had already been converted by the time the reactor reached temperature, time zero in FIG. 1. The primary product was that resulting from saturation of the phenolic ring, 2-methoxycyclohexanol (40% yield @ 1 h). Cyclohexanediol was the secondary product (8%), although cyclohexanol was also significant (4%). The methanol byproduct was found (1%). There was little phenol formed at this temperature. At 200° C. the initial conversion of guaiacol during heatup was 62%. As shown in FIG. 2 the methoxycyclohexanols were still the main product (38% yield @ 4 h), but cyclohexanediol became less important (3%) while more cyclohexanol was formed (8%). More methanol was present (2%), as was more phenol. At 250° C., 60% of the guaiacol was converted by the time the reactor reached temperature. As shown in FIG. 3 cyclohexanol almost surpassed methoxycyclohexanols as the main product. Methoxycyclohexanol yield peaked at 17% in the 1 to 2 h range before reacting on to secondary products. The maximum cyclohexanol yield was 13%. Cyclohexanediol was only a minor product (1%). More phenol was evident and cyclohexane became a significant product (2%); however, the hexane recovery is likely limited by its low solubility in the water. More cyclohexane may have been actually produced and remained in the reactor as a separate light phase, which could not be sampled by our method. Over the period of the test, the amount of aqueous phase products is reduced. A large methane gas product was produced in this test, as has been reported for processing at these conditions of temperature and catalyst wherein phenol was extensively gasified at as low as 250° C.[xi] At 300° C., phenol is the primary product that was recoverable. Cyclohexanol and methoxycyclohexanol are early products which are reduced to low levels within the first hour at temperature. All three isomers of methyl-phenol (cresols) are significant byproducts, as is benzene. Cyclohexane is present in the water product only at low concentration, but is likely present as a significant product in a separate phase. Because of the large amount of methane gas formation, this test was hydrogen limited with the reactor pressure surpassing the pressure set point after 1 h of operation and this factor is expected to have skewed the mechanism away from the high-use hydrogenation pathways, such as saturation of the aromatic ring.

[xi] Elliott, D. C.; Hart, T. R.; Neuenschwander, G. G. "Chemical Processing in High-Pressure Aqueous Environments. 8. Improved Catalysts for Hydrothermal Gasification." *Ind. Eng. Chem. Res.* 45(11) 3776-81, 2006.

The products from acetic acid were determined to be much more limited. Ethanol and ethyl acetate were attributed to hydrogenation of acetic acid. At 150° C. (see FIG. 4) there was only a small amount of ethanol formed (2%) with 85% of the acetic acid unreacted. Even at 200° C. (shown in FIG. 5) the ethanol yield was minimal (3%) while 84% of the acetic acid remained. However, at 250° C. there was strong evidence of reaction with 96% of the acetic acid converted as shown in FIG. 6. The ethanol product was formed with a maximum yield of 32% at 2 h and then was reacted further with only 8% remaining after 4 h. Ethyl acetate formation was not significant. A large methane product appeared to be the final product from acetic acid under these conditions, as it and the ethanol were nearly gone by the end of the test. This result is not surprising with the ruthenium catalyst, as has been found in other process development work on catalytic wet gasification at our laboratory[xii]. At 300° C. in this batch test mode, the acetic acid conversion to ethanol was actually less, apparently because of the hydrogen limitation and the large amount of gas (methane and carbon dioxide) formation.

[xii] Elliott, D. C.; Neuenschwander, G. G.; Hart, T. R. Low-Temperature Catalytic Gasification of Chemical Manufacturing Wastewaters: 1995-1998 Final Report. PNNL-11992, Pacific Northwest National Laboratory, Richland, Wash. 1998.

Furfural reacted quickly over the temperature range from 150 to 250° C. At 150° C., 83% of furfural was converted during heat-up to temperature. As shown in FIG. 7, the major product at 150° C. was tetrahydrofuran-methanol (THF-MeOH) at 8% with a lesser amount of γ-valerolactone (GVL) at 4%. 1,4-pentanediol (14PDO) was a lesser intermediate that was converted further to 2-methyl-tetrahydrofuran[xiii] (MTHF) with <1% remaining. The demethylated versions, γ-butyrolactone (GBL) and tetrahydrofuran (THF), were also found, as was 1,2-pentanediol (12PDO). As seen in FIG. 8, there was also a reaction pathway involving cyclopentanone as an early product that was subsequently hydrogenated to cyclopentanol and 1-pentanol. At the higher temperature of 200° C. 78% of the furfural was converted during the heat-up. As shown in FIG. 9, the THF-MeOH remained the major product (16%) but the GVL (4%), 14PDO (10%) and MTHF (2%) product slate became more prominent. The 12PDO was slightly more prominent but the GBL and THF were less so. As seen in FIG. 10, the cyclopentanone product was no longer present but cyclopentanol and 1-pentanol remained through the end of the test. At the higher temperature of 250° C. as seen in FIG. 11, 96% of the furfural was converted during heat-up. As shown in FIG. 11, the MTHF product became dominant (27%) along with its intermediates, GVL (22%) and 14PDO. The THF-MeOH product was formed initially (34%) but reacted further to a low of 3% @ 4 h, perhaps to the THF (10%). GBL, which was present early on, was similarly reacted to THF. The cyclopentanone pathway products represented in FIG. 12 was still evident but all three products were reacted further and no longer present by the end of the test, having probably broken down to methane. At 300° C. no furfural survived the heat-up period. The THF-MeOH product (10% yield at time 0) was reacted further and disappeared after the first sample. MTHF was the major product (38% @ 0.5 h) with THF as the important subsequent product. The reverse equilibrium product slate highlighted by GVL and levulinic acid[13] were also significant. The cyclopentanone product was found (12%) at time 0 but was reduced to trace quantities by 1.5 h. The subsequent alcohol products were not found.

[xiii] Elliott, D. C., & Fyre, J. G., Jr. (1999) Hydrogenated 5-Carbon Compound and Method of Making. U.S. Pat. No. 5,883,266.

Palladium Catalyzed Hydrogenations. In the case of palladium catalysis, the results were different. At 150° C., the primary product from guaiacol was 2-methoxycyclohexanone, resulting from a less complete saturation of the phenolic ring while a large portion of the guaiacol remained unreacted. Methoxycyclohexanol was found at only $\frac{1}{10}^{th}$ the concentration of the cyclic ketone. Cyclohexanediol was a lesser product, and cyclohexanol and phenol were almost insignificant. The methanol byproduct was found. At 200° C., shown in FIG. 13 the methoxycyclohexanols were the main product, but some cyclohexanediol was present. Cyclohexanol was slightly more prominent. More methanol was present. As seen in FIG. 14, at 250° C. methoxycyclohexanols were the main product, but significant guaiacol remained at the end of the test. Cyclohexanediol was a minor product. Cyclohexane was a noticeable product and slightly surpassed in quantity both cyclohexanol and phenol. Unlike the case of ruthenium catalysis, over the period of the test, the total amount of aqueous phase products appeared to remain nearly constant. At 300° C. the reaction of guaiacol through methoxycyclohexanol to cyclohexane was evident, as seen in FIG. 15. Methanol was the other significant product and became the major aqueous phase product by the end of the test. Phenol also played a larger role in the conversion process at this higher temperature than at the lower temperatures. Guaiacol was converted to almost 98% after the 4 hours at temperature. The total amount of aqueous phase products dropped by about ¾ths by the end of the test, suggesting that the major products were the volatile cyclic hydrocarbons.

Acetic acid did not appear to react over palladium catalyst at 200° C. (see FIG. 16) or below. As seen in FIG. 17, at 250° C. there was about a 5% yield of ethanol after 4 hours. At 300° C. the yield was increased to nearly 20% with a few percent of ethyl acetate formed as shown in FIG. 18. Unlike with ruthenium, there appeared to be little gasification of these products even at up to 300° C.

The furfural conversion chemistry was also much different for the palladium catalyzed case. Furfural reacted quickly at these conditions. It was found only in the initial samples from 150 and 200° C. tests. At 150° C. the main product was cyclopentanone. MTHF was present at slightly higher concentration than THF-MeOH. GVL was a lesser but significant product. As shown in FIG. 19, the MTHF and THF-MeOH were recovered from the 200° C. test at about the same concentration as at 150° C., but GVL was increased to the second most prevalent product. At the higher temperature of 200° C. the cyclopentanone product was noticeably converted to cyclopentanol, as seen in FIG. 20. At 250° C. MTHF was the largest product, as seen in FIG. 21. GVL and THF-MeOH were present in nearly equal amounts. Levulinic acid showed up early but was converted (to GVL) until it was gone by the end of the test. In FIG. 22 the transition was obvious from the early production of cyclopentanone with its subsequent conversion to cyclopentanol and the final product, 1-pentanol. At 300° C. (see FIG. 23) the early production of levulinic acid led quickly to GVL and MTHF formation. Similarly GBL and THF formation were significant throughout, though the GBL was gone by the end of the test. As seen in FIG. 24, 1-pentanol was the major product present at the end of the test.

The ruthenium catalysis of the aqueous phase reforming and methanation reactions limits its use to less than 250° C. for efficient hydrogenation chemistry. At higher temperature the formation of methane and carbon dioxide becomes the all-consuming reaction pathway. Since palladium does not catalyze the gasification reactions, it can be used at higher temperatures for hydrogenation.

Because of these differences there are different product slates achievable with the two catalysts. Acetic acid can not be effectively hydrogenated to ethanol with ruthenium. At the temperatures where there is significant activity, the gasification reactions were driving toward a final product of methane and carbon dioxide. On the other hand, we discovered, surprisingly, that acetic acid can be effectively hydrogenated to ethanol using a palladium catalyst at 300° C.

An important mechanistic route from furfural to cyclopentanone and pentanols was identified. At 250° C. and above with ruthenium catalyst, these products were gasified like the acetic acid and ethanol. The mechanism of furfural hydrogenation to tetrahydrofuran-methanol appears to be a final product for both ruthenium and palladium catalysis only at lower temperature. The pathway through γ-valerolactone (including some equilibrium-formed levulinic acid) to 1,4-pentanediol and methyl-tetrahydrofuran was more important at 250° C. and above.

As reported earlier for substituted guaiacols, the hydrogenation pathway using ruthenium catalysis passes through methoxycyclohexanol to cyclohexanediols at low temperature and continues on to cyclohexanol at higher temperature. At 250° C. and above the gasification reactions become dominant. In contrast, palladium catalysis leads first to methoxycyclohexanone at 150° C., methoxycyclohexanol at 200° C. with some cyclohexanediol. At 250° C. the product slate is shifted toward cyclohexanol and cyclohexane (without gasification), and by 300° C. the product slate is shifted strongly to cyclohexane with a large methanol byproduct.

EXAMPLES

Method for Batch Reactor Tests. A Parr 4562M 450 mL Hastelloy C pressure vessel was used for these reactions. The catalyst (5 g) was placed in the reactor with hydrogen gas at 4.2 MPa and reduced at 250° C. for 2 h, and then cooled. The catalysts were either a 3 wt % palladium on a carbon granule (12×50 mesh) produced by the incipient wetness method or 7.8 wt % ruthenium on carbon extrudates (1.5 mm) produced by Engelhard. A vacuum was drawn on the reactor and the liquid mixture (200 g) of 5 wt %, each of furfural, guaiacol (2-methoxy-phenol), and acetic acid, in water was pulled into the reactor vessel. The reactor was then pressurized to 6.9 MPa with hydrogen and heated to desired temperature. The solution was agitated with the turbine paddle stirrer at 1000 rpm throughout the test. The desired operating pressure of 13.8 MPa was set on the hydrogen gas regulator and maintained throughout the experiment. By this method hydrogen was added to the reactor as it was used in the reactions. For higher temperature tests, in which gasification occurred, the operating pressure went above the regulator setting and therefore no further hydrogen was added to the system and the chemistry was therefore hydrogen limited. In a single uncatalyzed test performed at 250° C., a solid, polymeric material formed from the furfural (no furfural was detectable at the end of the test) with a residual level of guaiacol and acetic acid in the aqueous phase similar to that in the feedstock. Liquid samples (2 g) were recovered by a sample dip tube at 0, 0.5, 1, 1.5, 2, 3, and 4 h. A purge sample was pulled before each collected sample, in order to make sure the sample lines were clear of residual product material. After the time of the test the system was cooled to room temperature, the residual gas product was vented, and a sample analyzed on a Carle series 400 GC. The offgas volume was measured through a wet test meter. Remaining liquid product was weighed along with the sample weights to get an over all mass balance.

Method of Product Analysis. Gas chromatography (GC) was performed with an Agilent model 6890 with a flame ionization detector (FID) to analyze the samples. Samples were run neat, if they were a single phase, typically only the later products. When two or more phases were present, acetone was added (1 mL) to dilute and bring the solution to one phase. The GC parameters included an injection size of 0.2 μL and an injection temperature of 260° C.; splitless injection was used. The temperature program started at 30° C.

and a 10° C./min ramp to 260°, then held for 5 min. A constant flow of 30 cm/sec was used with a starting pressure of 16.87 psig. The column used was an Agilent WaxEtr 60 m×320 μm with a 1.0 μm film thickness. The detector was set at 275° C. with 40 ml/min $H_2$ and 450 ml/min air. The carrier mode was constant with column and makeup flow combined for 45 ml/min; makeup gas was nitrogen.

Calibration was done with a 3-point calibration using the following components: phenol, cis-1,2 cyclohexanol, acetic acid, 2-methoxycyclohexanol, cyclohexanol, furfural, guaiacol, cyclohexanone, 2-butanol, ethanol, tetrahydrofuran, 2-methyl-tetrahydrofuran, cyclohexyl-methyl-ether. The standards were diluted in a 80/20 acetone/water solution. Uncalibrated components were given a semi-quantitative value based on similar components having the same number of carbon atoms.

Gas chromatography—mass spectrometry was used for qualitative analysis using an Agilent model 5890 GC running the same temperature program described above and the identical column, coupled with an Agilent model 5972 Mass Selective Detector (MSD). The MSD was scanning at a rate of 1.6 scans/sec from 20-500 atomic mass units. The mass data was analyzed using Agilent Chemstation software G1701AA version A02.00. The compound peaks were determined using a Probability-Based Matching (PBM) algorithm. Two libraries were used to identify peaks, the Wiley275 library (275,000 compounds) and an in house developed library of compounds we had determined from previous bio-oil analysis efforts[10]. A PBM library search proceeds by searching mass spectral libraries using the probability-based matching algorithm developed at Cornell University. The search algorithm compares an unknown spectrum to each reference spectrum using the reverse search technique. A reverse search technique verifies that the main peaks in a reference spectrum are present in the unknown spectrum.

Pyrolysis Oil Hydrotreating: Process Performance

The apparatus used for hydrotreating bio-oil in a continuous (not a batch) process was a fixed catalytic bed in a tubular reactor operated with concurrent down-flow of bio-oil and hydrogen gas. A bench-scale unit with a 400-milliliter fixed catalyst bed was assembled in our lab for process tests with different feedstocks, catalysts, and processing conditions. The bio-oil was fed to the reactor by a high-pressure metering piston pump. The pump's feed cylinder, feed lines, and the reactor were all maintained at temperature by a circulating hot oil system. Pressure in the reactor was maintained by a dome-loaded back-pressure regulator. Products exiting the reactor were cooled, and the condensed liquids collected in sampling cylinders, which were periodically drained. The gas product was vented through a meter, and intermittent samples were drawn for analysis.

During the tests using the palladium catalysts, the bio-oils were easily processed in the reactor system. The carbon-supported catalyst had 2 wt % palladium and an apparent bulk density of 0.5 g/mL. Processing temperature set points in the range of 200 to 360° C. were tested. A significant exothermic reaction caused the catalyst beds to operate at up to 20° C. higher than the set point.

Process Results

Tests were performed using a white softwood bio-oil obtained from Dynamotive, which during storage had separated into two phases. These tests proceeded smoothly with all reactor components functioning as designed. The process data are summarized in Table Y. The temperatures were measured temperatures, not the set point temperatures.

TABLE Y

Hydrotreating of Softwood Bio-oil, Heavy Fraction, with Edge-Coated 1.5% Pd/C Catalyst

| Run Conditions and Results | | | | | |
|---|---|---|---|---|---|
| Temperature, ° C. | 312 | 313 | 347 | 347 | 379 |
| Pressure, psig | 1910 | 1917 | 1911 | 1913 | 1939 |
| Liquid Hourly Space Velocity, L/L/hr | 0.22 | 0.22 | 0.22 | 0.22 | 0.22 |
| Carbon Balance, % | 94 | 83 | 94 | 92 | 90 |
| Material Balance, % | 96 | 93 | 97 | 97 | 94 |
| Product Yield, g/g of dry feed | 0.80 | 0.75 | 0.75 | 0.74 | 0.72 |
| Product Yield (mass balance normalized) g/g of dry feed | 0.83 | 0.81 | 0.77 | 0.76 | 0.77 |
| $H_2$ Consumption, L/L bio-oil feed | 156 | 232 | 296 | 237 | 319 |
| Deoxygenation, % | 48.2 | 52.0 | 61.3 | 58.7 | 65.3 |
| Water in oil, wt % | 4.93 | 5.44 | 2.91 | 2.91 | 2.16 |
| Aqueous phase carbon, wt % | 13.56 | 13.13 | 10.70 | 10.40 | 10.99 |
| Oxygen in dry oil, wt % | 16.99 | 17.61 | 12.52 | 14.28 | 12.52 |
| Density of product oil, g/mL | 1.122 | 1.087 | 1.03 | ~1.03 | 0.946 |
| Total Acid Number, mg KOH/g oil | | | 42.0 | | 36.5 |

Note:
Product Yield includes:
(1) Oil fraction of oil product (water free)
(2) Organics in aqueous phase.

What is claimed:

1. A product mixture made from a method comprising:
   providing a bio-oil;
   providing hydrogen (H2); and
   reacting the bio-oil and hydrogen over a catalyst at a temperature of more than 200° C.;
   wherein the catalyst comprises Pd; and
   producing a liquid oil from the reaction of the bio-oil and hydrogen.

2. A method of hydrogenation of furfural, guaiacol, or a substituted guaiacol, comprising:
   providing a liquid comprising furfural, guaiacol or a substituted guaiacol;
   providing hydrogen (H2); and
   reacting the furfural, guaiacol, or a substituted guaiacol with hydrogen over a catalyst at a temperature of more than 200° C.;

wherein the catalyst comprises at least 1 weight % Pd; and
converting the furfural, guaiacol or substituted guaiacol to a hydrogenated product.

3. The method of claim 2 wherein the liquid comprises guaiacol or a substituted guaiacol;
wherein the guaiacol or substituted guaiacol is reacted with hydrogen at a temperature of at least about 250° C.,
wherein the hydrogenated product comprises 2-methoxy-phenol or other cyclohexanol derivatives, and
wherein at least about 50% of the guaiacol or substituted guaiacols are converted to 2-methoxy-phenol or other cyclohexanol derivatives.

4. The method of claim 2 wherein the catalyst consists essentially of Pd disposed on a support.

5. The method of claim 2 wherein the liquid comprises furfural;
wherein the step of reacting the furfural with hydrogen over a catalyst is carried out at a temperature of at least 280° C.; and
wherein at least 5% of the furfural is converted to 1-pentanol.

6. The method of claim 2 wherein the liquid comprises furfural;
and wherein at least 6% of the furfural is converted to 2-methyl-tetrahydrofuran.

7. The method of claim 6 wherein the step of reacting the furfural with hydrogen over a catalyst is carried out at a temperature of at about 250° C. to about 300° C.

8. The method of claim 2 wherein the catalyst comprises 2 to 5 weight % Pd.

9. The method of claim 2 wherein the catalyst comprises Pd metal particles dispersed on a support selected from the group consisting of carbon, titania, and zirconia.

10. The method of claim 3 wherein about 50% to about 80% of the guaiacol or substituted guaiacols are converted to 2-methoxy-phenol or other cyclohexanol derivatives.

11. The method of claim 6 wherein at least 90% of the furfural is consumed by the reaction with hydrogen.

12. The method of claim 3 wherein the catalyst comprises at least 1 weight % Pd.

13. The method of claim 12 wherein the catalyst comprises Pd metal particles dispersed on a support selected from the group consisting of carbon, titania, and zirconia.

14. The method of claim 9 wherein the liquid comprises furfural; and wherein at least 6% of the furfural is converted to 2-methyl-tetrahydrofuran.

15. The method of claim 2 wherein the furfural, guaiacol or substituted guaiacol are present in a bio-oil.

* * * * *